(12) United States Patent
Pacey et al.

(10) Patent No.: US 8,529,442 B2
(45) Date of Patent: Sep. 10, 2013

(54) CHANNEL LARYNGOSCOPES AND SYSTEMS

(75) Inventors: John Allen Pacey, Vancouver (CA); Mitchell Visser, Burnaby (CA); Reza Ahmadian Yazdi, Richmond (CA); Yongkook Kim, Port Moody (CA)

(73) Assignee: Verathon Medical (Canada) ULC (CA)

( * ) Notice: Subject to any disclaimer, the term of this patent is extended or adjusted under 35 U.S.C. 154(b) by 269 days.

(21) Appl. No.: 12/947,746

(22) Filed: Nov. 16, 2010

(65) Prior Publication Data

US 2011/0178372 A1    Jul. 21, 2011

Related U.S. Application Data

(60) Provisional application No. 61/261,739, filed on Nov. 16, 2009, provisional application No. 61/319,835, filed on Mar. 31, 2010.

(51) Int. Cl.
 *A61B 1/267* (2006.01)
(52) U.S. Cl.
 USPC ............................ 600/188; 600/187; 600/199

(58) Field of Classification Search
 USPC .................. 600/185, 186, 188, 190, 194, 199
 See application file for complete search history.

(56) References Cited

U.S. PATENT DOCUMENTS 6,543,447 B2 *  4/2003  Pacey ....................... 128/200.26

* cited by examiner

*Primary Examiner* — Andrew Yang
(74) *Attorney, Agent, or Firm* — Richard Koske; P. G. Scott Born; Foster Pepper, PLLC

(57) ABSTRACT

Video-based laryngoscopes having an external centrally located channel coursing from the handle to a curved blade configured to deliver an ETT to a trachea as visualized by a non-removable, or alternatively, a removable video camera and lighting unit located beneath the external channel. The channel laryngoscope may be made for single use in a patient and discarded, or be processed for re-use. Alternatively, the channel laryngoscope may have a removable video camera and lighting member located within an internal chamber that runs parallel with the external channel. In another embodiment a laryngoscope adapter may be detachably affixable to the channel laryngoscope equipped with the non-removable camera to provide a decontaminated or sterile surface to permit re-use of the channel laryngoscope without having to undergo washing or decontamination procedures.

17 Claims, 33 Drawing Sheets

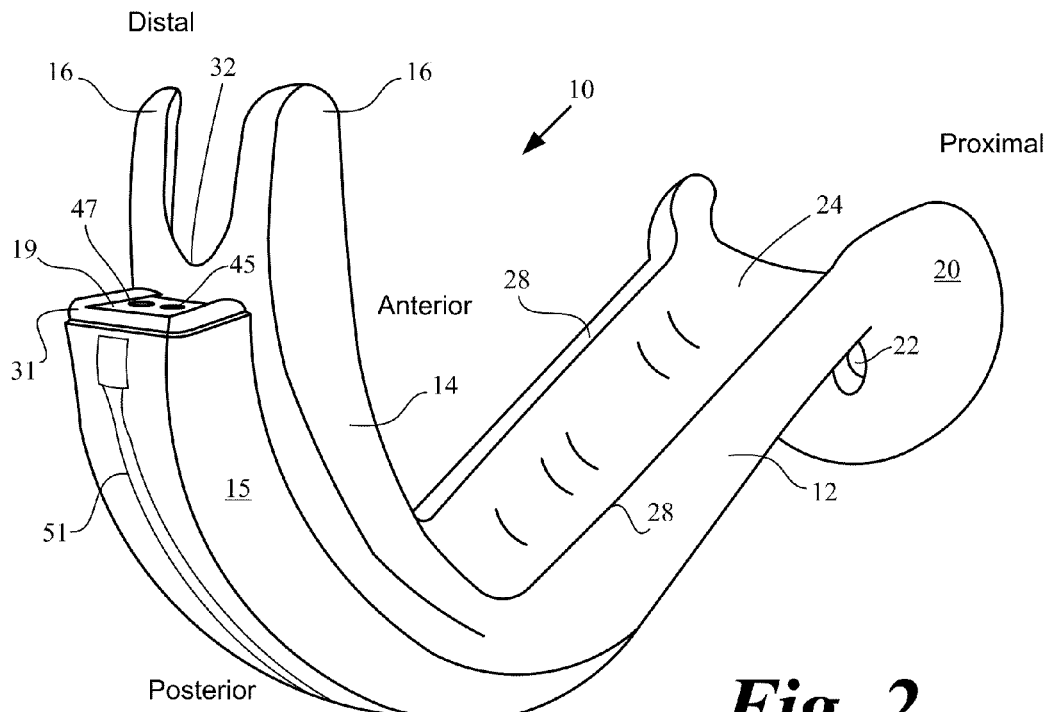
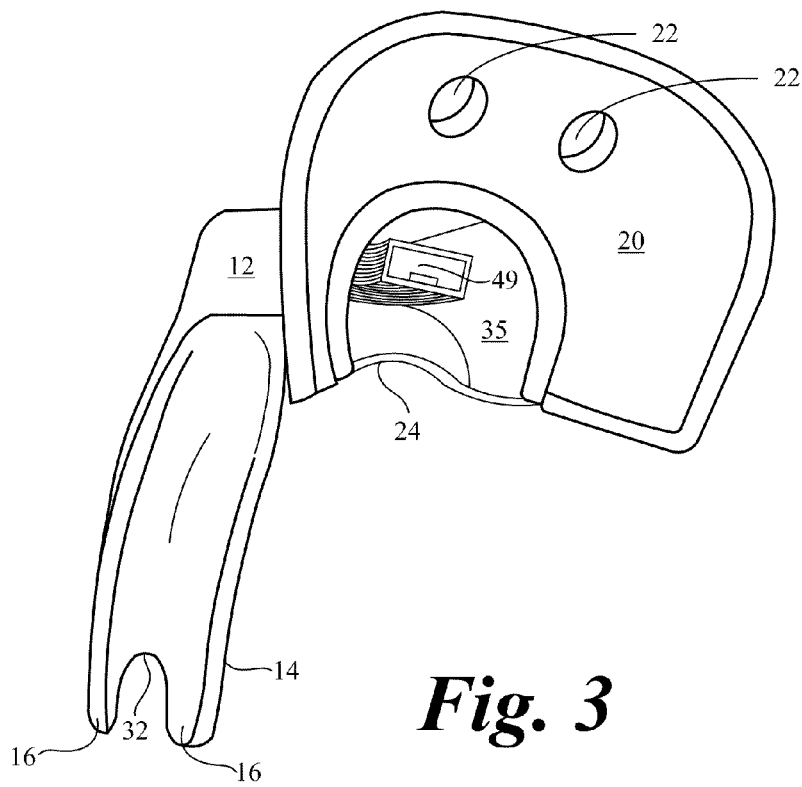

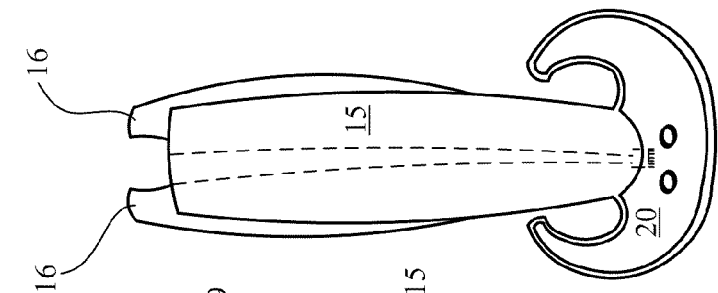
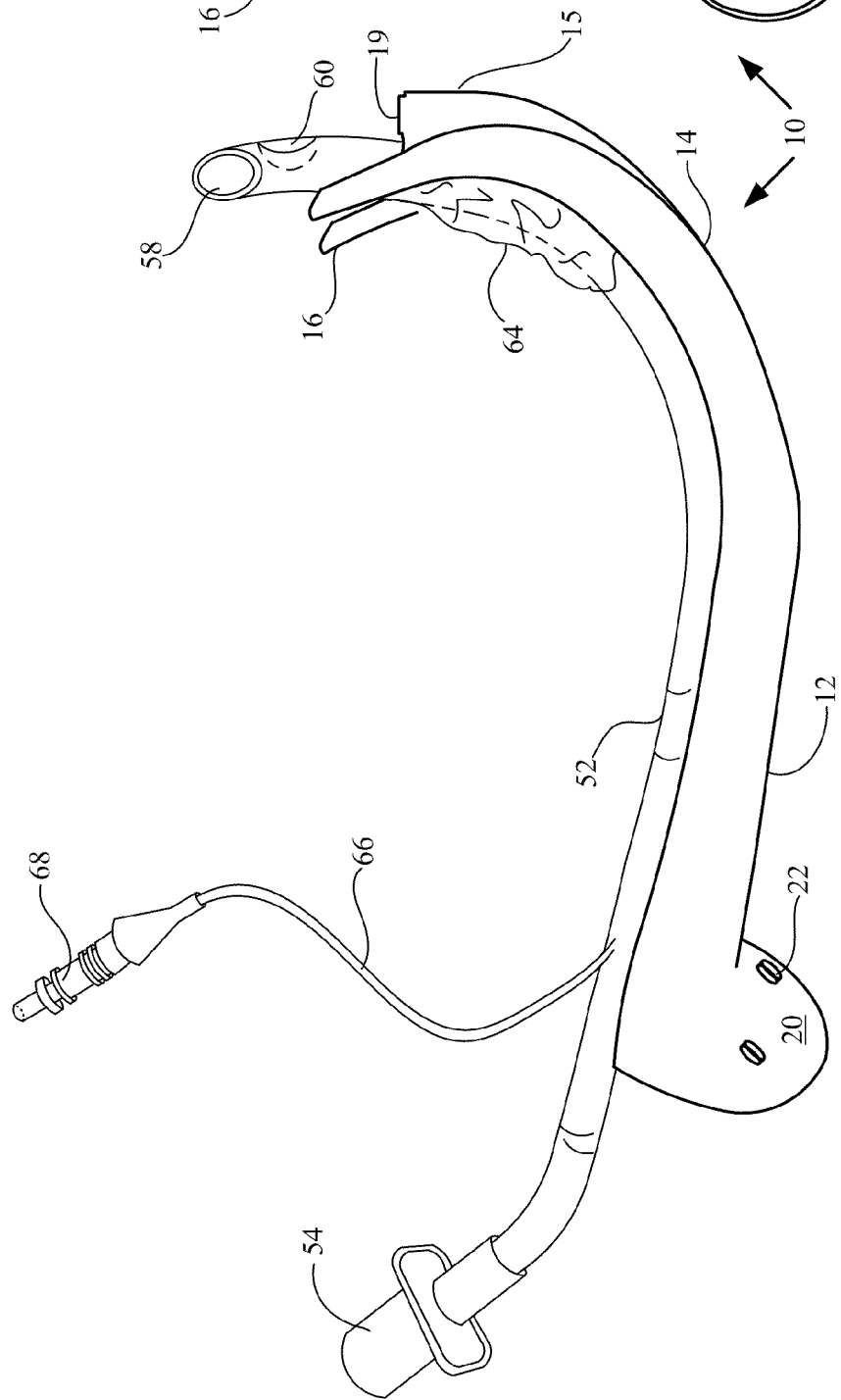

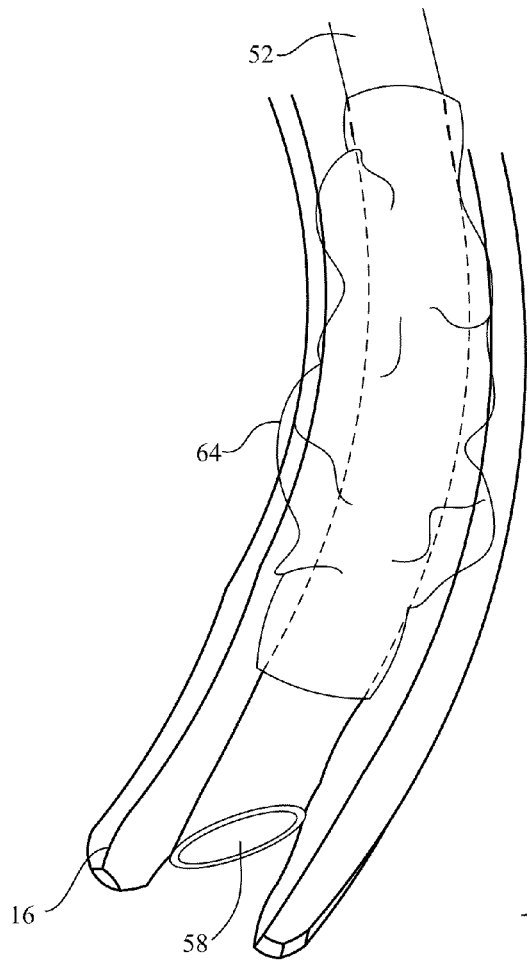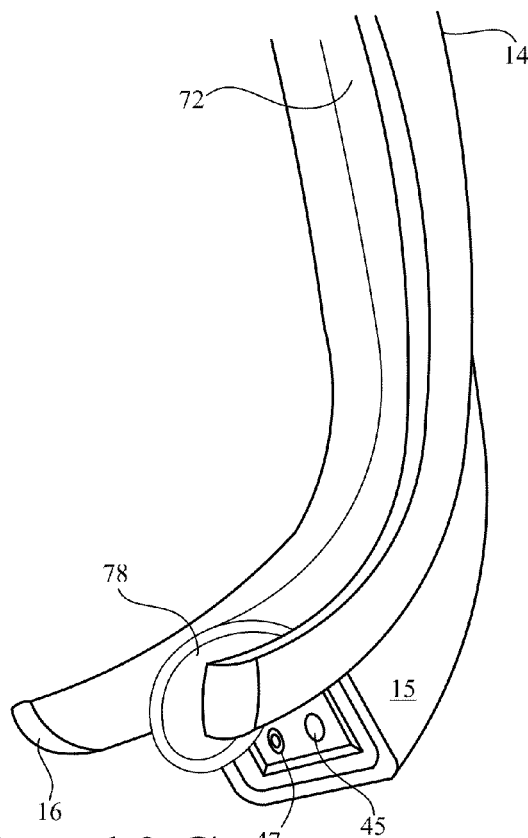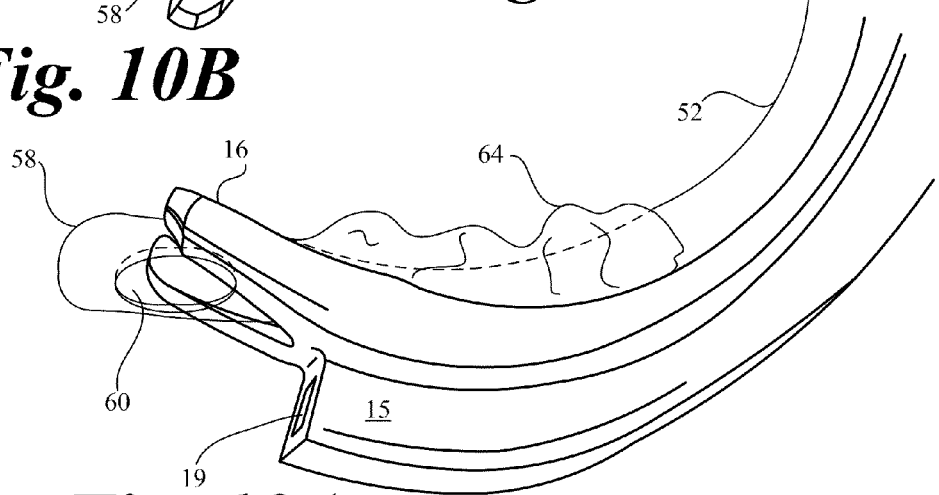
*Fig. 10B*
*Fig. 10C*
*Fig. 10A*

CHANNEL LARYNGOSCOPES AND SYSTEMS

CROSS REFERENCES TO RELATED APPLICATIONS

This application claims priority to and the benefit of the filing date of U.S. Provisional Patent Application No. 61/261,739 filed Nov. 16, 2009 and U.S. Provisional Patent Application No. 61/319,835 filed Mar. 31, 2010, both of which are hereby incorporated by reference in their entirety.

The application incorporates by reference in their entirety U.S. Pat. No. 6,142,144 filed Apr. 1, 1998 and its U.S. Provisional Patent Application Nos. 60/074,355 filed Feb. 10, 1998 and 60/067,205 filed Dec. 7, 1997; U.S. Pat. No. 6,543,447 filed Dec. 6, 2000 and its U.S. patent application Ser. Nos. 09/704,507 filed Nov. 2, 2007 and 09/060,891 filed Apr. 15, 1998; and U.S. Pat. No. 6,655,377 filed Jan. 30, 2003 and its U.S. patent application Ser. Nos. 09/732,129 filed Dec. 6, 2000 and 09/704,507 filed Nov. 2, 2000, and U.S. Provisional Patent Application Nos. 60/352,283 filed Jan. 30, 2002; 60/223,330 filed Aug. 7, 2000; 60/168,711 filed Dec. 6, 1999; 60/074,355 filed Feb. 10, 1998, and 60/067,205 filed Dec. 1, 1997. All patents and patent applications are incorporated by reference in their entirety.

FIELD OF THE INVENTION

Disclosure herein is generally directed to the field of airway management and examination of the upper airway, and, in particular, to apparatuses that permit examination of the upper airway and/or intubation.

BACKGROUND OF THE INVENTION

Endotracheal intubation provides the current preferred method for control of the airway for mechanical ventilation. The process involves passing an endotracheal tube (ETT) through the mouth, past the tongue, and to and through the vocal cords and larynx to seal the airway. This protects the patency of the airway and protects it from aspiration of gastric contents, foreign substances, or secretions. The complex and invasive procedure occurs regularly in surgery and emergency departments throughout the word. It is increasingly performed in pre-hospital settings such as ambulances, medical evacuation helicopters, and by military medics in combat and near-combat situations. It is well known that failure to intubate when required can lead to death or serious injury. Intubation is a complex process which presents numerous challenges, as well as myriad possible injuries to the patient short of death from de-oxygenation. In all instances, the better the view which the instrument of choice provides to the intubator, the lower the likelihood if error resulting in injury or death. Traditional laryngoscopes relied on opening the upper airway to allow a direct line of sight from the intubator's eye to the larynx. Subsequent developments in laryngoscopes utilized fiberoptic bundles, sometimes coupled to video displays. More recently, laryngoscopes with video cameras have made it possible to display the image of the airway anatomy from a position beyond the teeth, and in some instances allow the intubator to identify the relevant anatomical landmarks without repositioning the patient.

BRIEF DESCRIPTION OF THE DRAWINGS

Preferred and alternative examples of the present invention are described in detail below with reference to the following drawings:

FIG. 2 depicts a frontward perspective view of the channel laryngoscope;

FIG. 3 depicts a rearward perspective view of the channel laryngoscope;

FIG. 7 depicts a right side view of the channel laryngoscope with ETT;

FIG. 8 depicts a front view of the channel laryngoscope;

FIGS. 10A-D depict side perspective and top perspective views of the blade region of the channel laryngoscope with ETT in early stages of emerging from the channel guide;

DETAILED DESCRIPTION OF THE PARTICULAR EMBODIMENTS

Figure 1:
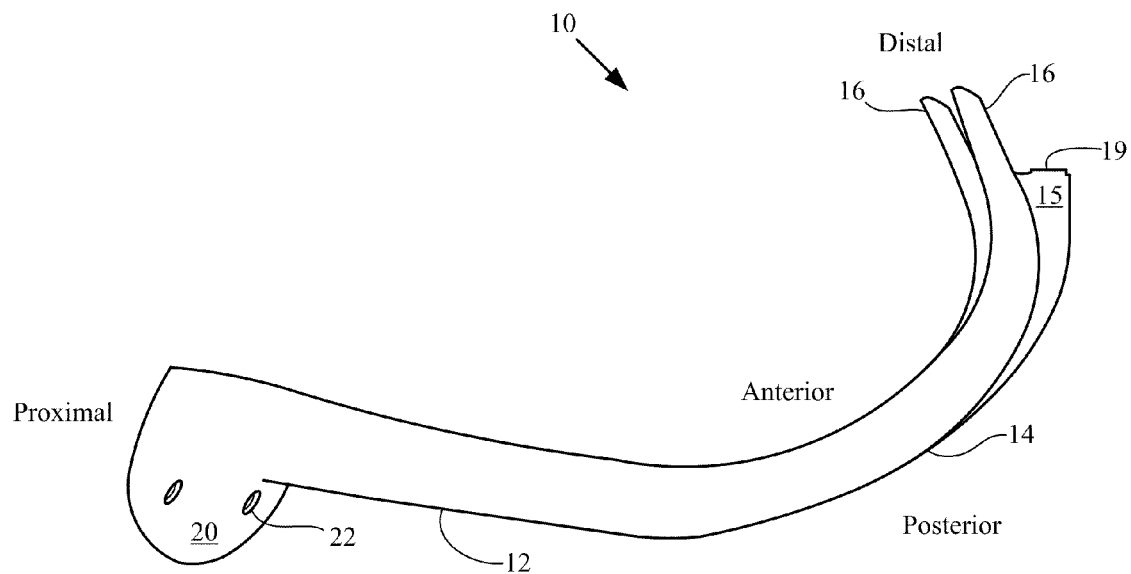
FIG. 1 depicts a side perspective view of a channel laryngoscope.

Several embodiments of a video-based intubation laryngoscope and system are described that allow for examination of the upper airway and intubation. The system employs video laryngoscope embodiments configured to hold and position an ETT for insertion into the trachea of a patient minimizing (reducing) the need for accessory stylets. Improved intubation speed and intubation accuracy is accomplished by the specific configurations in that unobstructed, real time or "live" views are immediately obtained on a viewable display monitor. The laryngoscopes configurations described herein provide an aiming aid that allows real time re-positioning of the video laryngoscope to optimally align the tip of the ETT with the glottic aperture just prior to advancing the ETT through the glottis from the video laryngoscope. The video laryngoscopes provide clear, direct images of the larynx, vocal cords, and laryngeal area on the display monitor and offer a means to control the trajectory of the ETT toward and through the glottic aperture.

The laryngoscope includes an external centrally located channel coursing from the handle to a blade configured to deliver an ETT to the glottic aperture which is visualized by a video camera and lighting unit located on the posterior side of the laryngoscope blade, directed towards the distal end. The video-based channel laryngoscope embodiments may be made with materials that allow for sterilization and re-use, or alternatively, be configured to include a disposable portion which houses a removable video camera and lighting member located within an internal chamber. The removable video camera and lighting member unit is sufficiently sealed within the internal chamber to prevent moisture or fluids from reaching the internal optical electronics of the video camera and lighting member. In yet another embodiment a disposable laryngoscope adapter or sheath may be detachably affixable to the channel laryngoscope equipped with the non-removable camera to provide a clean to sterile surface which permits re-use of the video-based channel laryngoscope without having to undergo washing or decontamination procedures.

The channel laryngoscope includes an external centrally located channel coursing from the handle to a curved blade for holding and delivering an ETT. Images of the upper airway anatomy are captured by the video camera occupying the internal channel running substantially parallel to the external channel and connected to a video monitor. The non-removable camera in the channel laryngoscope is preferably made with materials which can withstand required cleaning and/or sterilization procedures, so that after use it is cleaned and decontaminated to enable sanitary use in another patient. In an alternative embodiment, the laryngoscope with embedded video camera is designed to be discarded after a single use, for use in, e.g., situations where cleaning, decontaminating, and/or sterilization is impractical due to use-in-the-field logistical complications, such as in military campaigns undertaken in hostile environments. For users other than the military, it may also be preferable to utilize a single-use, disposable embodiment that is constructed in a single piece.

Descriptions and figures described below with regard to multiple embodiments of a video-equipped channel laryngoscope that is configured to hold an ETT within the centrally located external channel that courses from the handle to the blade for delivery to a patient's trachea. The blade is structured to fit within the oropharynx and extend to the hypopharynx and glottic aperture. It is sufficiently rounded to pass over the posterior portions of the patient's tongue without undue tissue compression or extensive manipulation of the head and neck. Intubation is visualized by a camera system mounted beneath the centrally located channel and connected to a video monitor. One embodiment of the video-based laryngoscope utilizes a non-removable camera system which is preferably re-usable and requires that the channel laryngoscope be cleaned, decontaminated and/or sterilized before re-use.

Alternatively, for use in multiple patients without having to clean or decontaminate the laryngoscope, another embodiment utilizes a detachably affixable laryngoscope adapter that provides a clean covering or sheath. The laryngoscope adapters intended for single use are also known as a sheath. After delivery of an ETT to the trachea, the laryngoscope adapter or sheath is removed, discarded, and replaced with a new laryngoscope adapter for use in the next patient, thereby avoiding having to wash or decontaminate the laryngoscope before using in different patients. The laryngoscope adapter may be provided as decontaminated or, alternatively, sterilized units suitable for use in larygnoscopic procedures.

Yet another embodiment is a laryngoscope sheath having the external centrally located channel and a central chamber running parallel beneath the external channel in which the central chamber is configured to detachably hold a removable camera and light source member. The same video camera member may be used in various different sized laryngoscope sheaths designed for use in differently sized patients, e.g., child and adult sized sheaths. The laryngoscope sheath may be discarded, or, depending on material construction, subjected to rigorous cleaning, disinfection, and/or sterilization processes for re-use with the removable camera and lighting electronics.

Additional details for the alternate embodiments provide for a laryngoscope equipped with a light source and video camera that is connected with a display monitor. The laryngoscope is configured to hold, position, and deliver an ETT to and through the glottic aperture from a centrally located exterior channel. The exterior channel courses continuously through the linear handle portion and curved blade portion of the video-based laryngoscope. Beneath the external channel is a video camera and light source located near the end of the blade region. The camera and light source are positioned within the laryngoscope to obtain a sufficient field of view to assist in intubation of a patient's trachea. The positioning of the camera may be substantially co-linear with the external channel to obtain a centered view of the glottic aperture with sufficient perspective to see pertinent structures surrounding the glottic aperture that might have a bearing on the intubation procedure, for example the location of the epiglottis and vocal cords. The centrally located external channel terminates distally with a pair of tube guides. A space or notch between the tube guides forms a channel guide which serves to maintain the centered delivery of an emerging ETT from the centrally located channel. In alternate embodiments a retaining members may partially or fully span the external channel to retain the ETT within the external channel. Such retaining members could be placed near the proximal end of the channel, or distally near the base of the lifter tips, spanning the end of the notch at the far distal end, or at multiple locations between the proximal and distal ends of the channel.

In use, the laryngoscope together with an ETT placed in the channel, is introduced into a patient's oropharynx. The user holds the laryngoscope and ETT firmly in one hand (typically the left hand) thereby ensuring that the ETT advances together with the laryngoscope. The channel holds the ETT generally in the midline of the instrument, with the tip of the ETT positioned to pass distally between the tube guides in the channel formed by the gap between the tube guides. The patient's tongue presses against the ETT, assisting in holding the ETT in mid-line position. As the laryngoscope and ETT are together advanced and rotated into the hypopharynx and distally towards the larynx, the camera will capture a substantially centered view of the patient's upper airway, including, as the laryngoscope is advanced and the epiglottis is lifted, the glottic aperture, vocal cords, and beginning of the trachea. This view will be displayed on the display monitor in real time, and, in alternate embodiments, may be recorded or broadcast to another location. The user can adjust the laryngoscope's position as required to align the tip of the laryngoscope, and thus the tip of the ETT, with the center of the glottic aperture. Once the glottic aperture is identified on the monitor, the ETT is advanced from the external channel, the tip of the emerging tube is seen and its alignment relative to the glottic aperture is ascertained on the monitor. The user then gradually advances the aligned and centered ETT and observes on the video display the progress of the ETT into and past the vocal cords in into the trachea. The shape and position of the ETT is advantageously optimized by the laryngoscope blade so that the ETT may be inserted into the trachea without using an assistive device such as a stylet or bougie.

The intubation laryngoscope may be equipped with non-removable or removable video electronic components that are appropriately sealed from fluid intrusion. If the video camera and light source are non-removable, then the laryngoscope can be carefully cleaned and/or subjected to decontamination procedures that do not damage the video camera and associated electronics. Alternatively, the entire laryngoscope including the non-removable electronic components, can be covered with a disposable cover so that the laryngoscope may be re-used with a new cover but without cleaning and decontamination. If the video camera and light source are removable, then the laryngoscope sheath can be cleaned and decontaminated with procedures that might otherwise damage the camera and associated electronics. Alternatively, the sheath can be discarded after a single use in a patient.

Also described below are alternate embodiments for the video-based intubation laryngoscope having non-removable electronics in which it is desired to use the same laryngoscope in sequential, multi-use scenarios between different patients without having to undergo a cleaning and/or decontamination or sterilization cycle of the laryngoscope. The alternate embodiments include a laryngoscope adapter or a sheath adapter having a hard portion and a flexible covering portion connected with the hard portion. The hard portion snaps to the terminal end of the curved blade and the flexible covering is wrapped over the remaining blade region and the handle to provide the video-based intubation laryngoscope with a clean or sterile covering for use in the next examination or intubation procedure of a new patient. After examination or intubation the used sheath adapter may be removed from the video-based laryngoscope with non-removable electronics and discarded. Another new and clean or sterile sheath adapter can be removeably affixed to the laryngoscope for use in another patient.

Other embodiments provide for a disposable or re-useable sheath that includes a hard, transparent region and a flexible cuff extending from the hard region. The hard region of the sheath adaptively fits over the terminal portion of the blade and the flexible cuff may be rolled to fit over the remaining portion of the blade and laryngoscope handle. The sheath covered laryngoscope can thus be used in a different patient without subjecting the laryngoscope to time consuming washing and decontamination procedures.

The detachable component video laryngoscope or the disposable or re-useable sheath may have a substantially central trough to hold an ETT for delivery during laryngoscope procedures. The central trough may terminate at the distal end with guide extenders to help direct the ETT to its intended location.

Other embodiments encompass reusable video laryngoscopes having flexible cameras that are insertable into transparent or non-transparent disposable sheaths having optically clear viewing windows. The reusable video laryngoscopes are configured to be detachably secured by locking tabs located in the transparent or non-transparent disposable sheaths with complementary posts and ledges of the video laryngoscopes. Other securing means can be used, such as complimentary shaped components that allow snug friction fits between surfaces. For example, a single or series of convex-shaped pegs can be inserted into companion concave-shaped receptacles for friction fitting attachment that provides enough retaining force to enable the operation of the laryngoscope and still allow for rapid detachment by the user after laryngoscope operation. One friction fit device could include rubber grommets that provide a grabbing like action to keep detachable sections sufficiently attached during a laryngoscopic procedure.

Embodiments and alternate embodiments are described with detail with reference to the FIGS. 1-31. The laryngoscope embodiments illustrated and described below may be appropriately sized and dimensioned to fit the anatomy of infant, pediatric, and adult patient populations. Additionally, the laryngoscope channel can be formed to properly restrain and guide the appropriately sized ETT corresponding to the patient population for which the laryngoscope is intended. For example, ETTs as small as 3.0 mm are available for use in infants, and in correspondingly larger sizes such as 6.0 to 6.5 mm ETT for pediatric patients, 7.5 to 8.0 mm ETT for adult female patients, and 8 to 8.5 mm ETT for adult male patient. The ETT may be single lumen or double lumen, and may include an inflatable and deflatable cuff.

FIGS. 1-12 depict a channel laryngoscope 10 having embedded video electronics that are not readily removable but advantageously provides the centering and delivery of ETTs in a single hand held device. As the non-removable video electronics cannot be subjected to extreme heat exposure conditions commonly used in autoclave-based sterilization procedures, the channel laryngoscope 10 undergoes cleaning and/or decontamination procedures before using in different patients.

FIG. 1 depicts a side perspective view of a channel laryngoscope 10. The channel laryngoscope 10 includes a handle 12 and a blade 14. The handle 12 is straight. The blade 14 is curved to accommodate the curvatures of the oropharynx and posterior tongue portions of a patient. At the proximal end of the handle 12 is a handle grasp 20 with a pair of accessory apertures 22. The blade 14 includes a concave disposed anterior region and a convex disposed posterior region. The concaved disposed anterior region of the blade 14 is the tongue contact side of the laryngoscope 10. The convex disposed posterior region of the blade 14 when placed in a patient's oral cavity faces the hard and soft palates. The anterior region is configured to hold an ETT that is further discussed in FIGS. 2-12 below. At the distal end of the blade 14 is a pair of tube guides 16. The tube guides 16 are designed to retain the ETT within the long axis of the anterior region. The tube guides 16 also displace the epiglottis either by lifting it directly or by activation of the hyo-epiglottic ligament to reveal the glottic aperture as described in FIGS. 24 and 25. Substantially co-linear along the lengthwise axis of the channel laryngoscope 10 is a video electronics chamber 15 that is positioned on the posterior side of the channel laryngoscope 10.

FIG. 2 depicts a frontward perspective view of the channel laryngoscope 10. Between the tube guides 16 is a distally located notch 32 along which an ETT exits during an intubation procedure. Within the midline of the anterior portion of the channel laryngoscope 10 resides an externally disposed channel 24 that courses from proximally located handle grasp 20 to the distally located notch 32. The channel 24 is bracketed by ridges and extends into the blade 14. The blade 14 may be constructed of non-ferrous magnetic resonance imaging (MRI) compatible materials and is curved and terminates distally at notch 32. The notch 32 is flanked by the pair of tube guides 16 that are continuous with the ridges 28 and form in the gap between them the notch 32. The channel 24 is trough-like and in alternate embodiment can be sized to accommodate ETTs of various sizes, appropriate to the intended patient size for the laryngoscope. Substantially co-linear along the lengthwise axis of the channel laryngoscope 10 is seen the video electronics chamber 15 that runs below and parallel to the channel 24. A window plate 19 resides at the terminal end of the video electronics chamber 15. Beneath the window 19 is a light source 45 and video camera 47. A sealing frame 31 secures the window plate 19 to the video chamber 15 and keeps the light source 45 and video camera 47 isolated from liquid contact associated with the patient's oropharynx. The thickness of the sealing frame 31 may be approximately 1 mm. Other dimensions relating to the positions of the light source 45, video camera 47, and other components are described in FIG. 10E below. When the video chamber 15 is constructed of clear plastics, the electronic pathway 51 is seen residing within the video chamber 15. An electronic pathway 51 resides within the video chamber 15 and can be seen with the video chamber 15 is made of transparent materials. The electronic pathway connects the light source 45 and video camera 47 with the video circuit connector 49. The video circuit connector 49 is described in FIG. 3 below.

The distal end as shown is split into two tips 16, which are sized and shaped to displace the epiglottis either by lifting it or by activating the hyo-epiglottic ligament as described in FIGS. 24 and 25 below. The tips 16 form between them the notch 32 which guides the ETT through the centerline of the notch defined between the tips 16. In alternate embodiments, the blade 14 can be designed in such a way that it can be detachably mounted to the handle 12.

FIG. 3 depicts a rearward perspective view of the channel laryngoscope. Between the handle grasp 20 and channel 24 is a video electronics chamber 35 that resides internally within the video electronics chamber 15 shown in FIG. 2. Extending proximal from the electronics chamber 35 is a video circuit connector 49. The video circuit connector establishes electrical power and image circuit contacts for the light source 45 and video camera 47 with the display monitor 310 shown in FIGS. 26-31 below.

Figure 4:
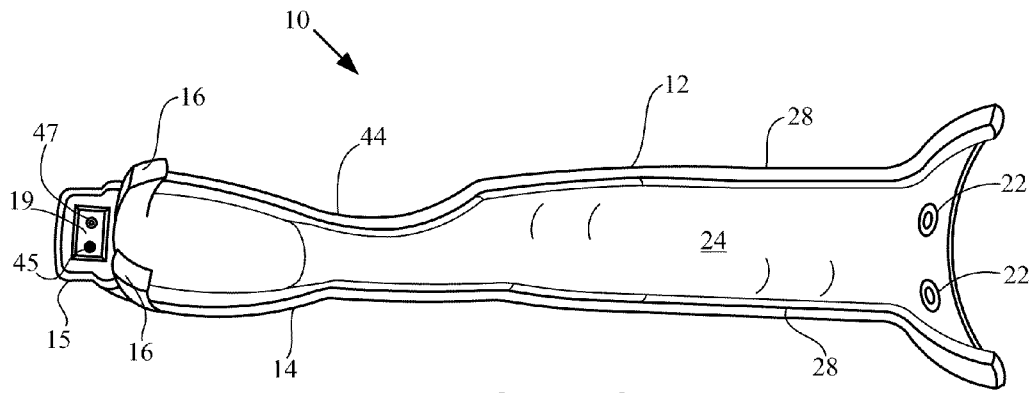
FIG. 4 depicts a top view of the channel laryngoscope.

FIG. 4 depicts a top view of the channel laryngoscope 10. Ridges 28 are shown coursing the length of the handle region 12 and blade region 14 and combining with the tube guides 16 extending distally from the blade region 14. A blade indent 44 provides an asymmetric configuration and to narrow the blade region 14 to serve to assist handling of the laryngoscope 10 within the confined spaces of the upper airway.

Figure 5:
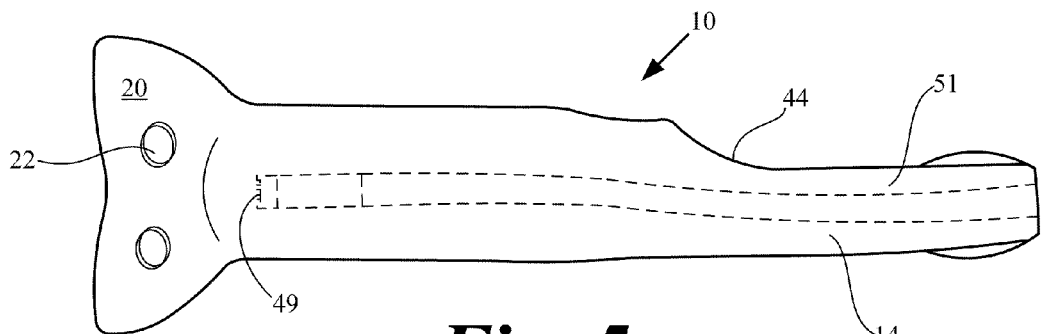
FIG. 5 depicts a bottom view of the channel laryngoscope.

FIG. 5 depicts a bottom view of the channel laryngoscope 10. The electronic pathway 51 (dashed lines) resides within the video chamber 15 and connects the light source 45 and video camera 47 with the video circuit connector 49. The asymmetric configuration conferred by the blade indent 44 also narrows the blade region 14 for easier handling of the channel laryngoscope 10 within the confined space of the upper airway.

Figure 6:
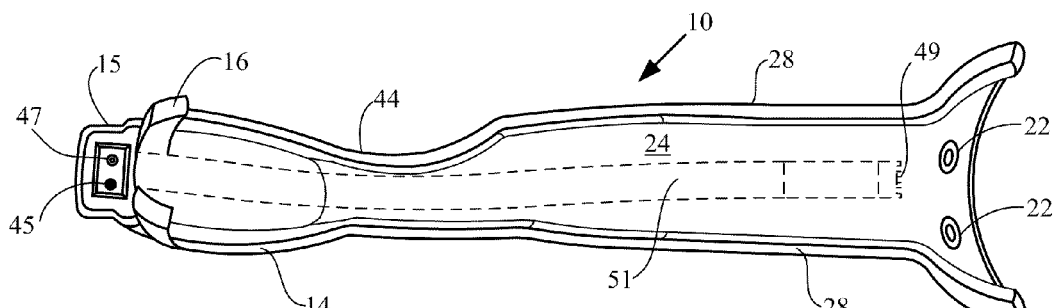
FIG. 6 depicts another top view of the channel laryngoscope showing electronic pathway of video camera and illumination circuitry.

FIG. 6 depicts another top view of the channel laryngoscope 10 showing the electronic pathway 51 connecting the light source 45 and video camera 47 with the video circuit connector 49.

FIG. 7 depicts a right side view of the channel laryngoscope with an ETT partially exiting the notch 32. The ETT 52 includes a hose connector 54, terminal aperture 58 and side aperture 60. The side aperture 60 is also known as a "Murphy's Eye". Extending between tube guides 16 of the blade region 14 the ETT 52 is shown to acquire a curvature amenable to following a trajectory to the glottic aperture GA. An inflatable cuff 64 is not yet emerging past the distant ends of the channel guides 16. The ETT 52 extends within the channel 24 from the handle region 12 to and beyond blade region 14. Air tube 66 is hydraulically connected with the inflatable cuff 64 and conveys air injected from gas port 68.

FIG. 8 depicts a front view of the channel laryngoscope. The channel or tube guides 16 are shown extending beyond the video circuitry chamber 15.

Figure 9A:
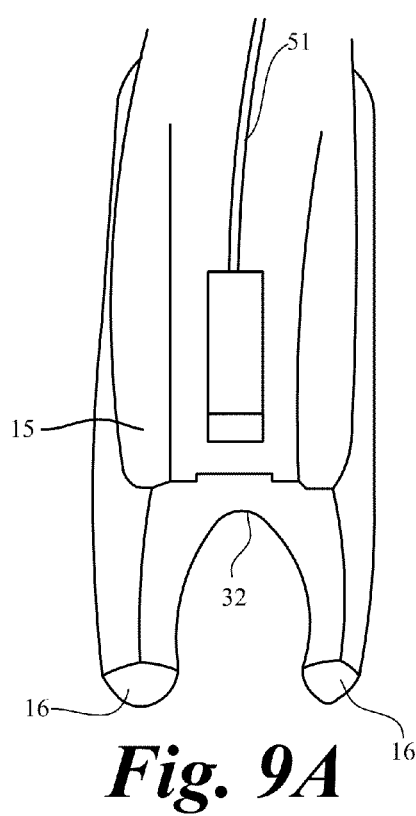
FIGS. 9A-C depict front, top, and perspective side views of the blade region of the channel laryngoscope.
Figure 9B:
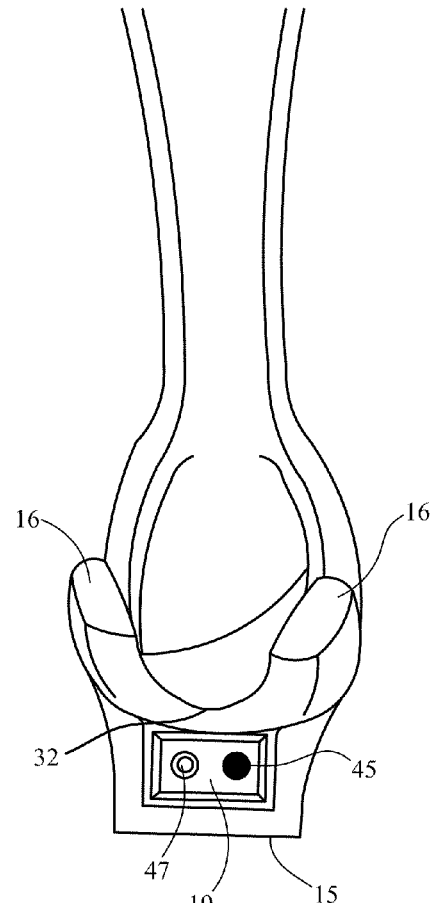
Figure 9C:
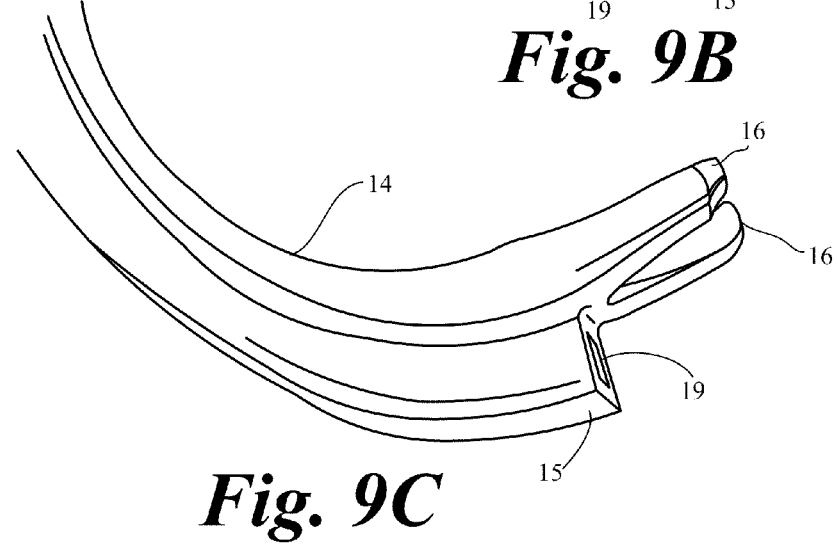

FIGS. 9A-C depict front, top, and perspective side views of the blade region of the channel laryngoscope. Light source 45 illuminates the laryngopharynx to reveal the glottic aperture for intubation. The position of the camera 47 relative to the notch 32 allows for early visualization of the ETT 52 emergence from the notch 32 and its positional confinement between tube guides 16.

Figure 10D:
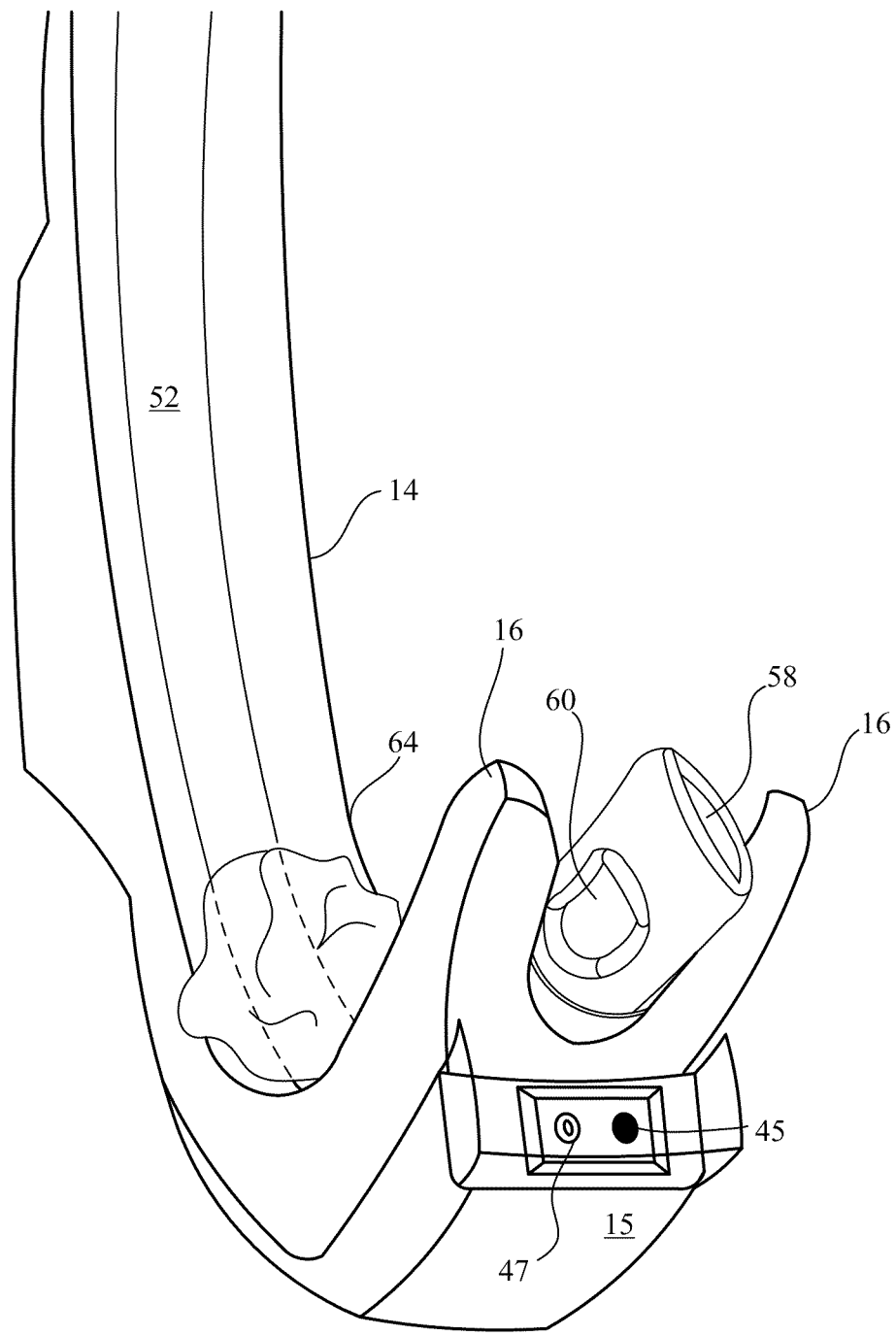

FIGS. 10A-D depict side perspective, top perspective views, and a front cross-section view of the blade region of the channel laryngoscope with ETT 52 in early stages of emerging from the channel or tube guides 16. Early stage emerging is shown to be within the field of view of the video camera 47. FIGS. 10A and 10D depict the side aperture 60 emerging between channel guides 16 about midway of the side aperture's 60 length.

Figure 10E:
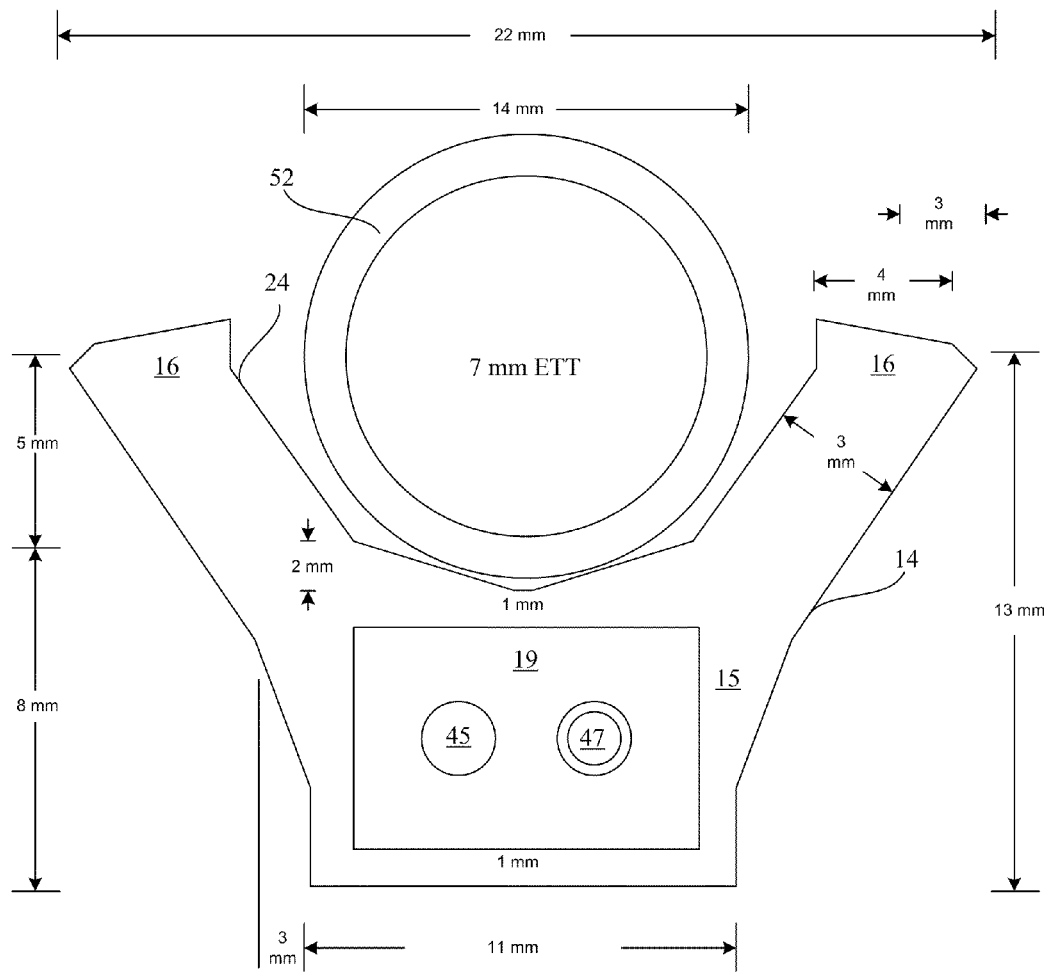
FIG. 10E depicts a front cross-section view near the distal end of an embodiment of the channel laryngoscope.

FIG. 10E depicts a front cross-section view near the distal end of an embodiment of blade region 14. A 7 mm representative ETT 52 is shown cradled near the end of the blade region 14 within channel 24 having a 2 mm cradle height. The video chamber 15 includes a base of approximately 11 mm. Channel or tube guides 16 flanking the channel 24 are shown having an approximate 3 mm thickness and to be separated from extreme side to extreme side by approximately 22 mm between the beveled corners of the channel guides 16. The top portion of channel guides 16 is approximately 4 mm and the distance from the midway portion of the top of the channel guide 16 to the end of the beveled corner is approximately 3 mm. The height from channel guide 16 to base of the video chamber 15 is approximately 13 mm and comprises a 5 mm channel guide height to the upper 2 mm cradle height and an 8 mm separation to the base of the video chamber 15. The window 19 is centered by about 1 mm from the bottom of channel 24 and the base of video chamber 15. Light source 45 and camera 47 are shown behind the window 19.

Figure 11:
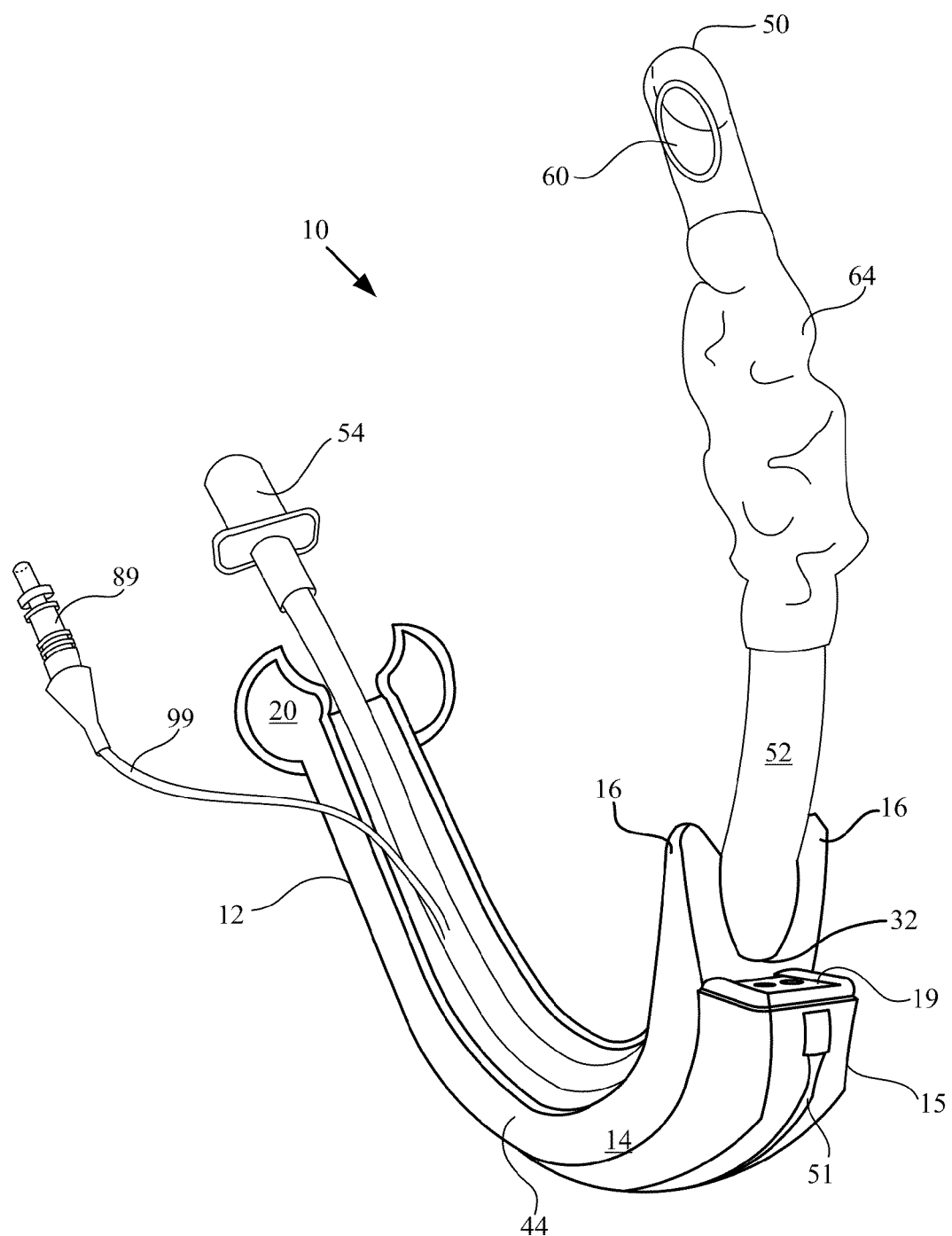
FIG. 11 depicts a side perspective view of the channel laryngoscope with ETT in later stage emerging from the channel guide.

FIG. 11 depicts a side perspective view of the channel laryngoscope with ETT in later stage emerging from the channel guide.

Figure 12:
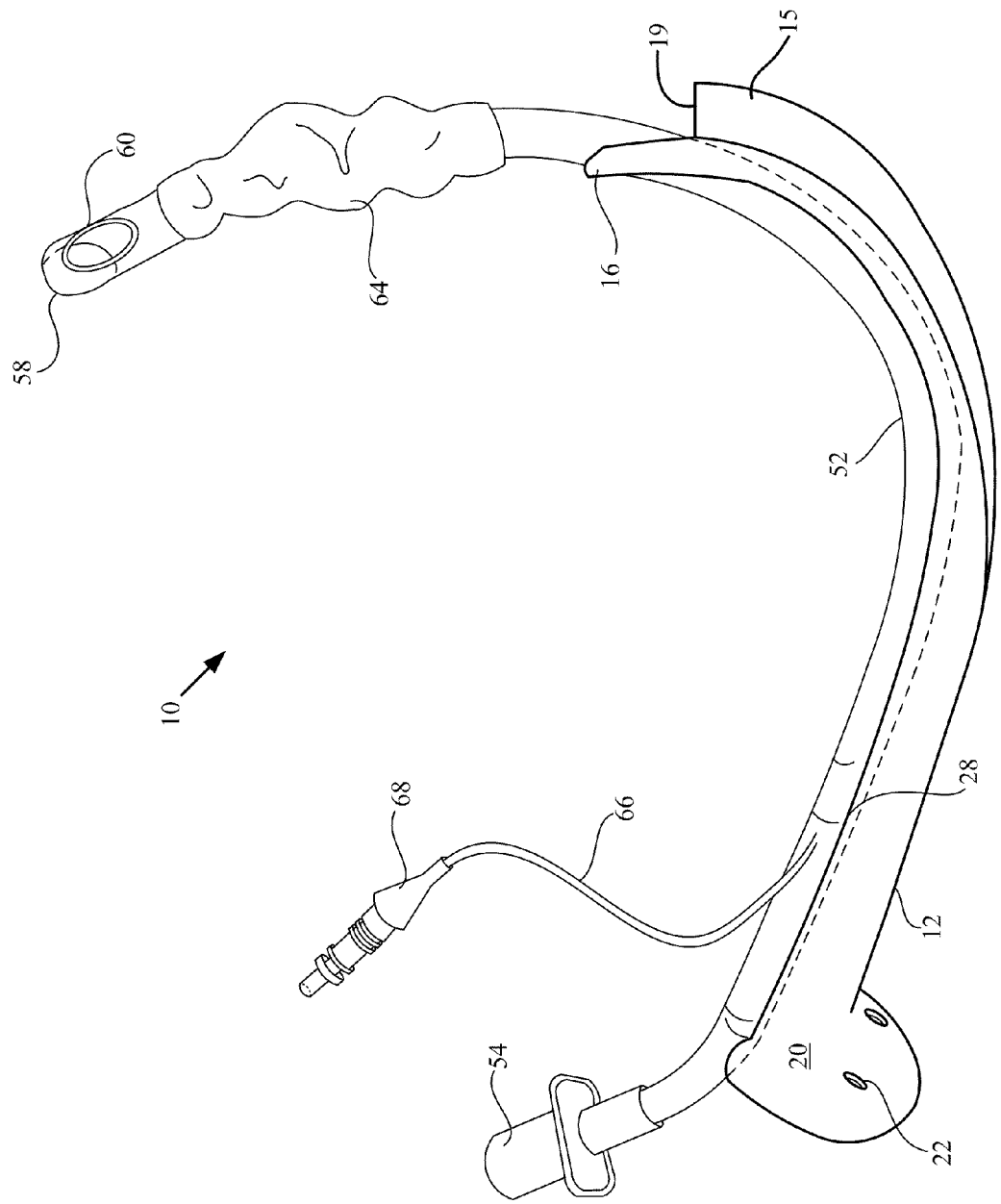
FIG. 12 depicts a side view of the channel laryngoscope with ETT in later stage emerging from the channel guide.

FIG. 12 depicts a side view of the channel laryngoscope with ETT in later stage emerging from the channel guide or tube guide 16 from the blade region 14. A substantial curvature to the ETT 52 is conferred by the curvature of the blade region 14 so that the ETT 52 may acquire a trajectory to more easily allow tube 52 to be directed to the trachea without requiring a stylet occupying the lumen region of the ETT 52.

Figure 13:
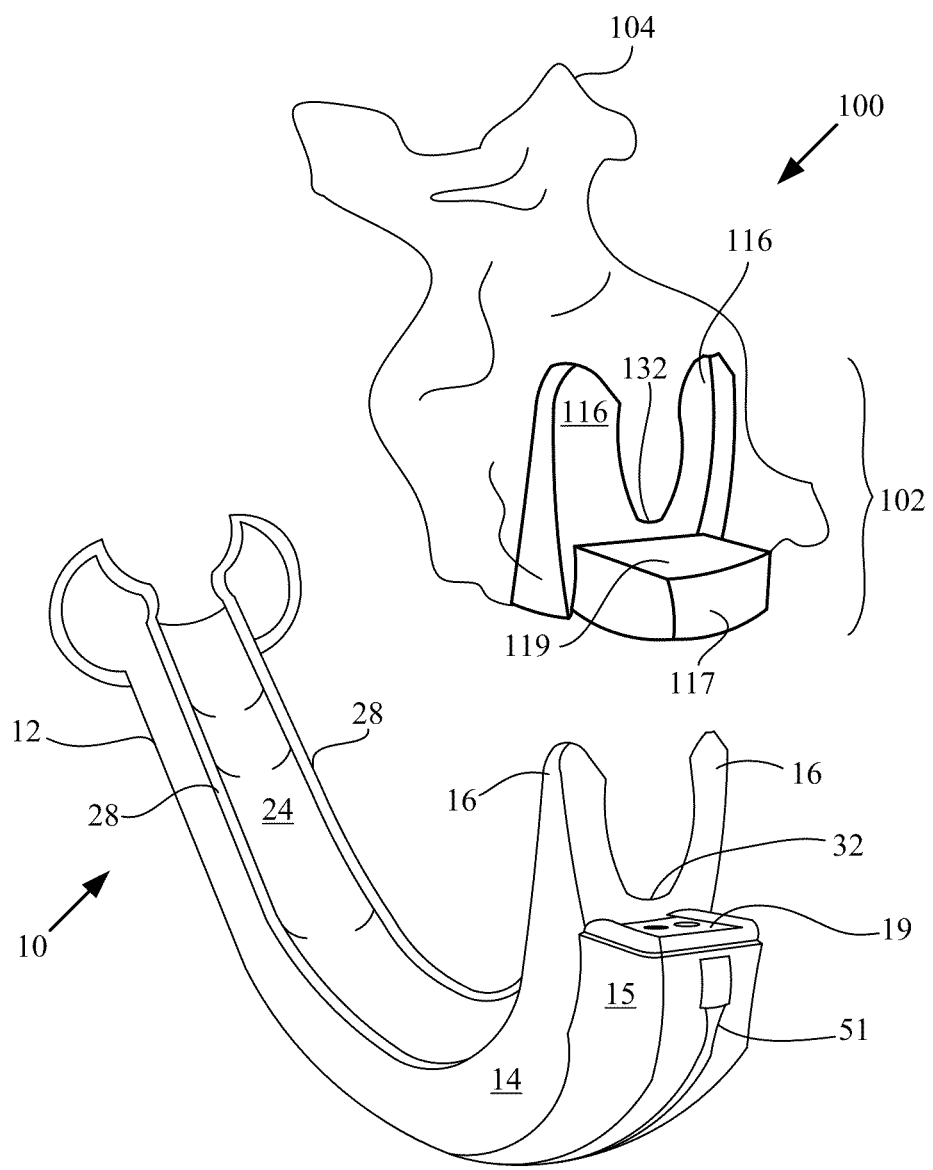
FIG. 13 depicts a side perspective view of a dual component sheath having a hard shell connected with a flexible sock-like cover in positional alignment for attachment to the blade tip region portion of the channel laryngoscope.
Figure 14:
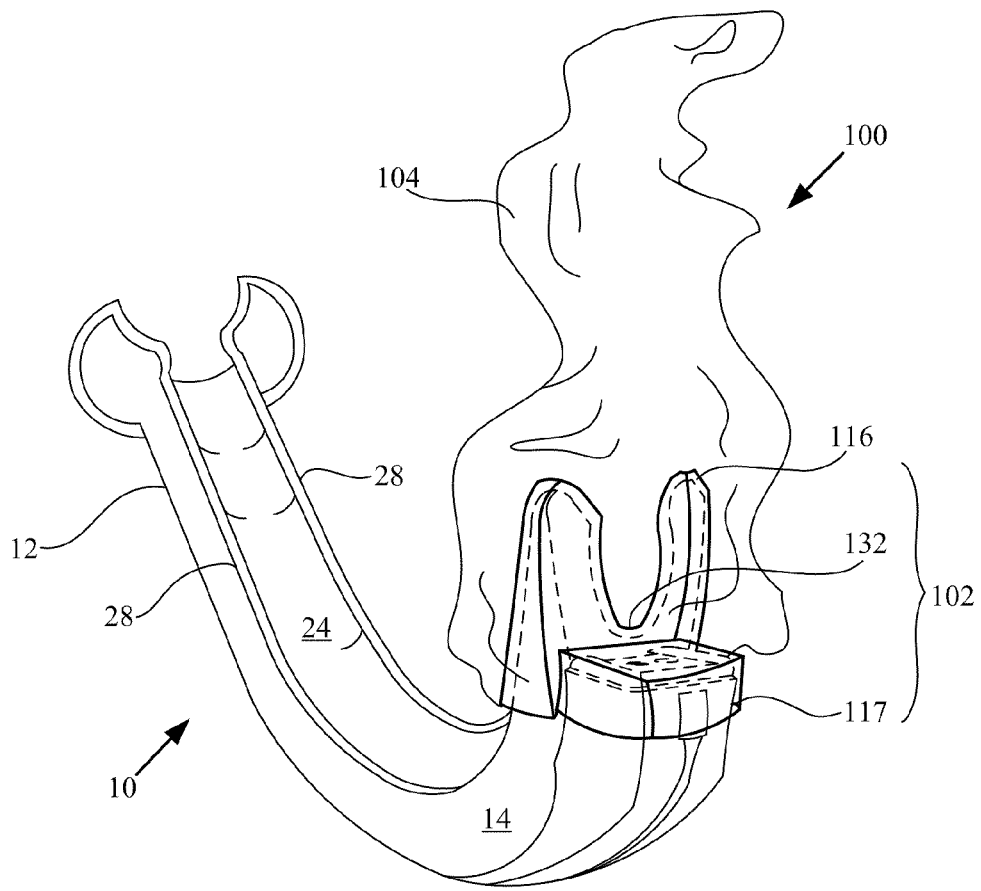
FIG. 14 depicts a side perspective view of the dual component sheath having the hard shell portion attached to the blade tip region portion of the channel laryngoscope.
Figure 15:
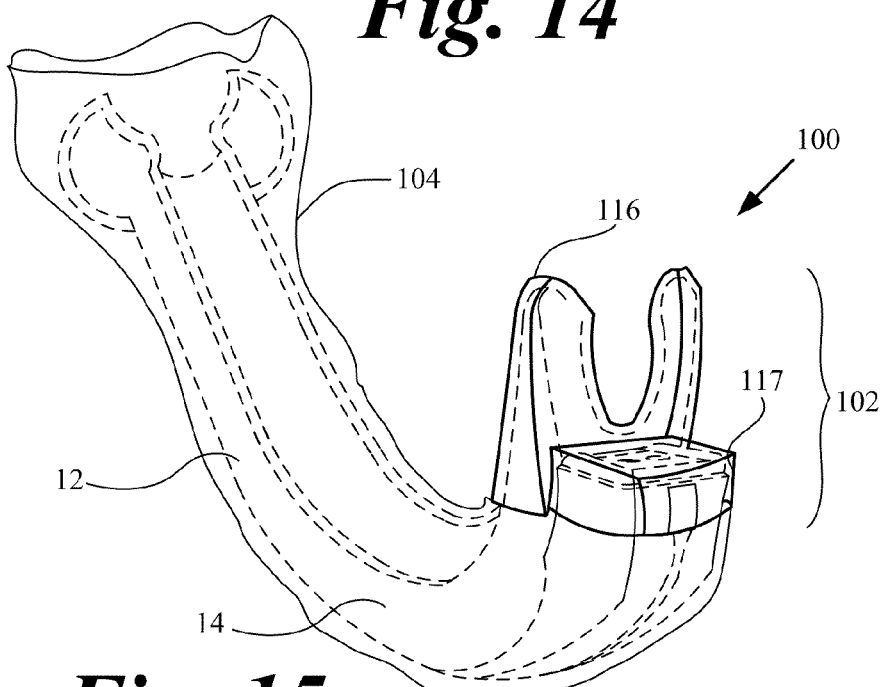
FIG. 15 depicts a side perspective view of the dual component sheath in which the sock-like cover is inverted over the remaining portions of the channel laryngoscope.

FIGS. 13-15 illustrates a sheath 100 detachably affixable to the laryngoscope 10 having non-removable video electronics. The sheath 100 provides use of the ETT by a single hand held device without having to undergo cleaning and/or decontamination procedures of the channel laryngoscope 10 between different patients.

FIG. 13 depicts a side perspective view of a sheath 100 having dual components including a hard shell cap 102 connected with a flexible sock-like cover 104. The hard shell cap 102 and sock-like cover 104 are designed to sheath the distal, middle, and proximal regions of the channel laryngoscope 10 to allow sequential use of the laryngoscope 10 between different patients in which the dual component sheath 100 is fitted before insertion of the channel laryngoscope 10 into a new patient. As shown the hard shell cap 102 is depicted in positional alignment for attachment to the blade tip region portion of the channel laryngoscope 10.

The hard shell cap 102 is similarly shaped and a slightly larger version of the distal components of the channel laryngoscope's 10 channel guides 16, notch 32, and optical plate 19. The hard shell cap 102 includes channel guides 116, notch 132, and plate cover 120 that are proportionally dimensioned about 1 mm larger or otherwise sized to allow a complementary snap fitting of channel guides 116 with guides 16, notch 132 with notch 32, and optic plate 119 with camera plate 19. The hard shell cap 102 is preferably transparent, and the optical plate 119 of high transparency to allow the video camera 47 to acquire a lighted field view of the trachea T illuminated by the light source 45. Attached to the hard shell cap 102 is the sock-like cover 104. The sock-like cover 104 may be a thin plastic material having a transparent or non-transparent nature.

FIG. 14 depicts a side perspective view of the sheath 100 having its hard shell cap 102 portion attached to the blade tip region portion of the channel laryngoscope 10. The sock-like cover 104 is not yet wrapped over the remaining blade portion 14 and the handle region 12 portions of the channel laryngoscope 10.

FIG. 15 depicts a side perspective view of the dual component sheath 100 in which the sock-like cover is inverted over the remaining portions of the channel laryngoscope 10 to provide a clean or sterile covering to the laryngoscope 10 before insertion into the oropharynx of the next patient. After using in an observational and/or intubation procedure, the sheath 100 may be removed, discarded and rapidly replaced with a new sheath 100 allowing efficient, sequential re-use of the laryngoscope 10 by avoiding having to undergo intervening decontamination and cleaning procedures.

FIGS. 16-19 illustrate alternate channel-shaped sheath embodiments in which the optical electronics are removable to allow transfer to new channel-shaped sheaths for sequential use of the removable electronics between different patients so that the video electronics are not exposed to harsh and time consuming decontamination, cleaning, and/or sterilization procedures. The external channel-sheath embodiments are configured as laryngoscope chamber members that may be disposable or washed, decontaminated, and/or sterilized to permit re-use with affixably detachable video camera and lighting members. The video or lighting members, or video wands, are insertable within the internal chamber that runs parallel with the external channel that holds the ETT.

Figure 16:
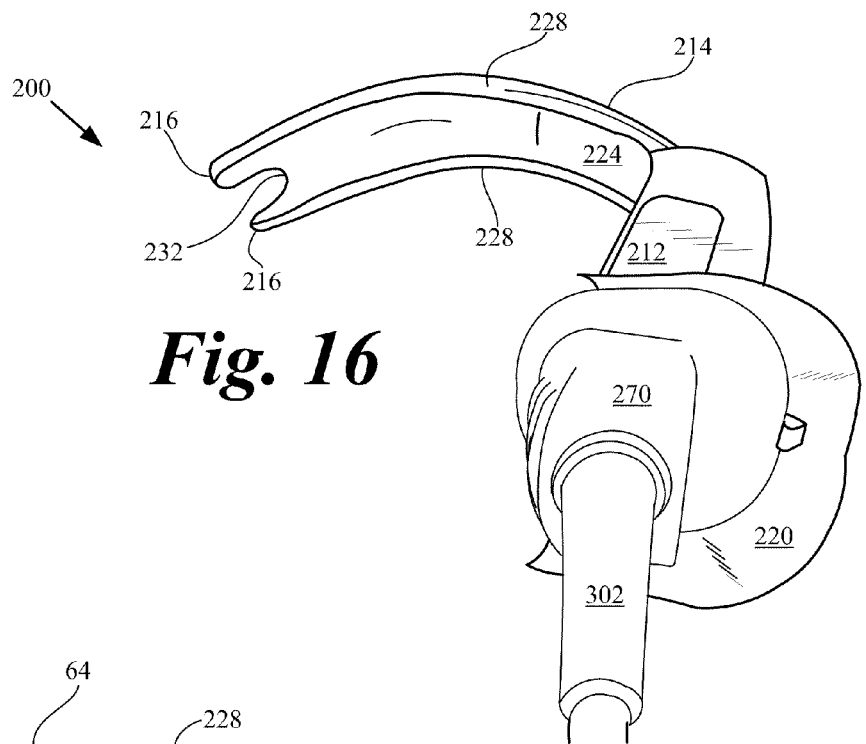
FIG. 16 depicts a rearward perspective view of an alternate embodiment of the channel laryngoscope with removable optical electronic wand positioned within the channel laryngoscope.

FIG. 16 depicts a rearward perspective view of an alternate embodiment of the channel laryngoscope 10 described in FIGS. 1-12 that comprises an integral, hard shell channel laryngoscope sheath 200. Hard shell channel sheath 200 comprises a replaceable hard shell cover in which a removable optical electronic wand 270 having video optical fiber electronics is removable from the channel sheath 200. The video wand 270 is affixably detachable from the channel sheath 200. The channel sheath 200 includes a centrally located channel 224 to advantageously hold and deliver ETTs 52 or 72 between ridges 228. The channel ridges 228 continue to form channel guides 216 that extend beyond notch 232. The video wand 270 is orientated centrally parallel to the long axis of the centrally disposed channel 224. Cable 302 conveys signals to an adjacent monitor for image display.

Figure 17:
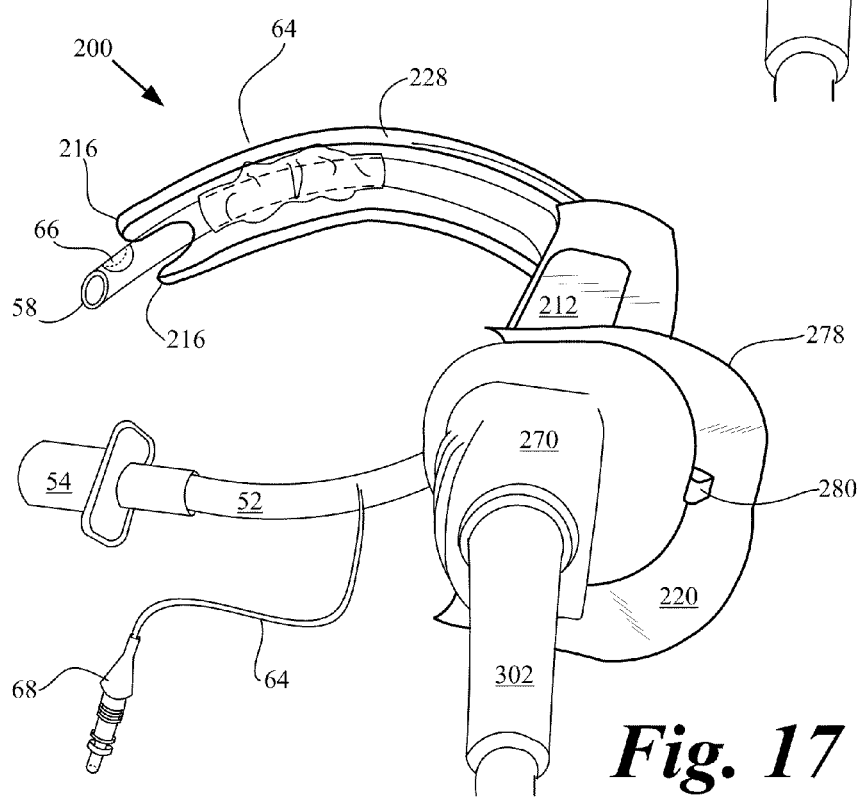
FIG. 17 depicts a rearward perspective view of the alternate embodiment of the channel laryngoscope of FIG. 16 with ETT.

FIG. 17 depicts a rearward perspective view of the alternate embodiment of the channel laryngoscope of FIG. 15 with ETT 52. The video wand 270 is retained by snap clasp 280 affixed to handle grasp 220 to securely keep the video wand 270 from slippage. The snap clasp 280 flexes enough to allow the video wand 270 to easily detach with application of slight pulling forces, and to re-engage the outer lip 278 of the video wand 270 when the wand 270 is pushed into the internal chamber 215, illustrated in FIG. 17 below, of channel sheath 200.

Figure 18:
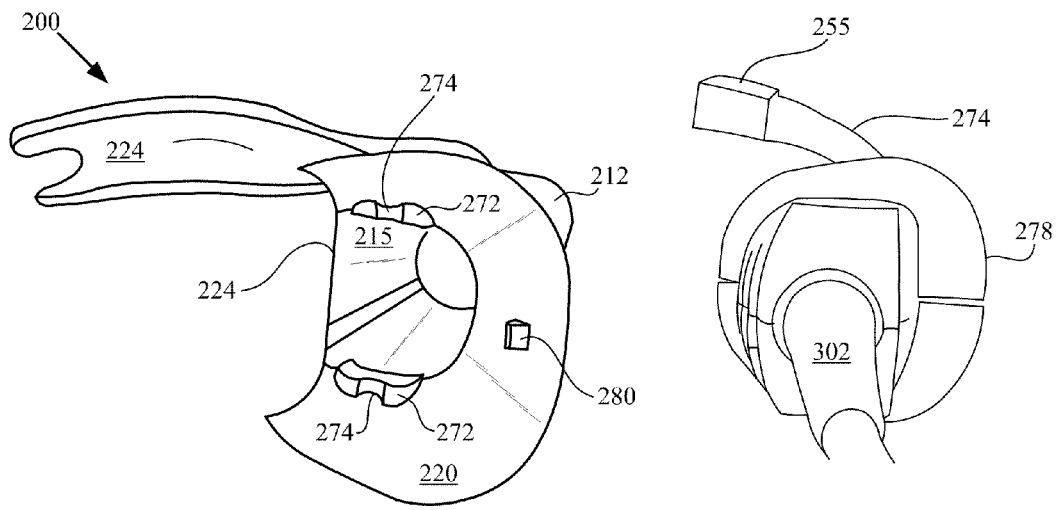
FIG. 18 depicts a rearward perspective view of an alternate embodiment of the channel laryngoscope with removable optical electronic wand detached from and placed adjacent to the alternate channel laryngoscope.

FIG. 18 depicts a rearward perspective view of an alternate embodiment of the channel laryngoscope 200 with removable optical electronic wand 270 detached from and placed adjacent to the alternate channel laryngoscope 200. Here the exterior channel 224 is shown extending into the handle region 212 and the internal chamber 215 that houses the video wand 270. Ledges 272 include pin receptacles 274 to receive alignment pins (not shown) located on the sides of video wand 270.

Figure 19:
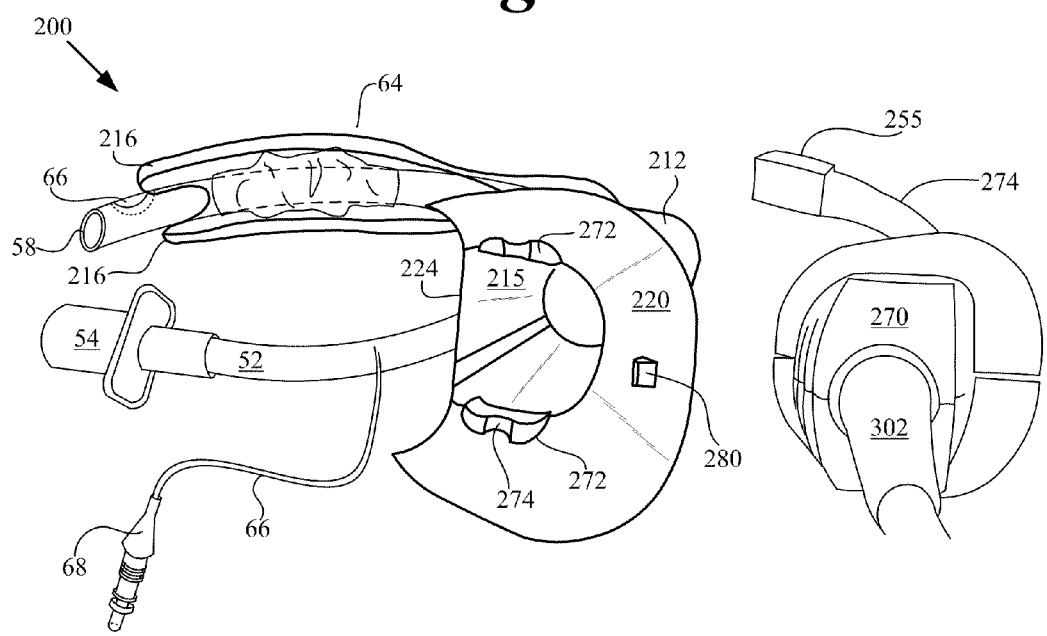
FIG. 19 depicts a rearward perspective view of an alternate embodiment of the channel laryngoscope of FIG. 17 with ETT.

FIG. 19 depicts a rearward perspective view of an alternate embodiment of the channel laryngoscope 200 of FIG. 18 with ETT 52.

Figure 20:
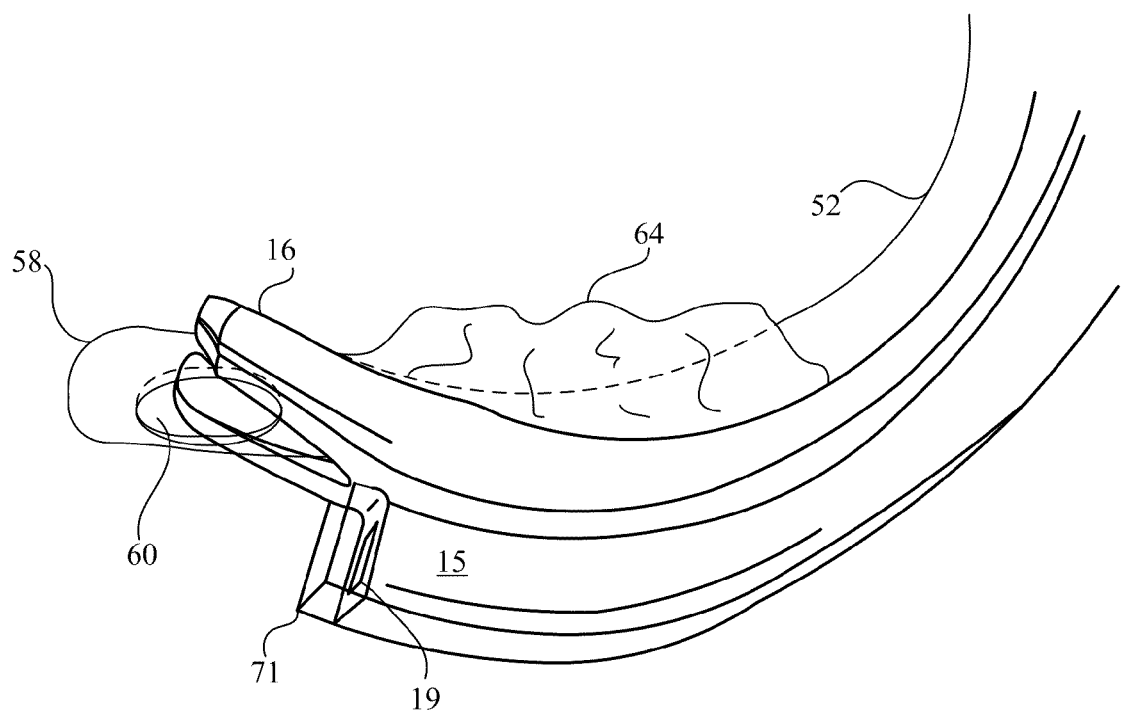
FIG. 20 depicts an alternate embodiment of channel laryngoscope 10 having a canopy that circumscribes the window.

FIG. 20 depicts an alternate embodiment of the channel laryngoscope 10 having a canopy 71 that circumscribes the window 19. The canopy 71 is three-sided and open-ended. The canopy 71 extends the exterior portion of the electronics chamber 15 so that the window 19 is recessed and protected from, e.g., sputum, vomit, gastric fluids, or other material obstructing the window 19 during intubation and/or examination of the airway by the barrier action provided by the three sides of the canopy 71. The minimization of fluid obstruction of the window 19 by the canopy 71 reduces the frequency and severity of image blurring obtained by the camera 47.

Figure 21:
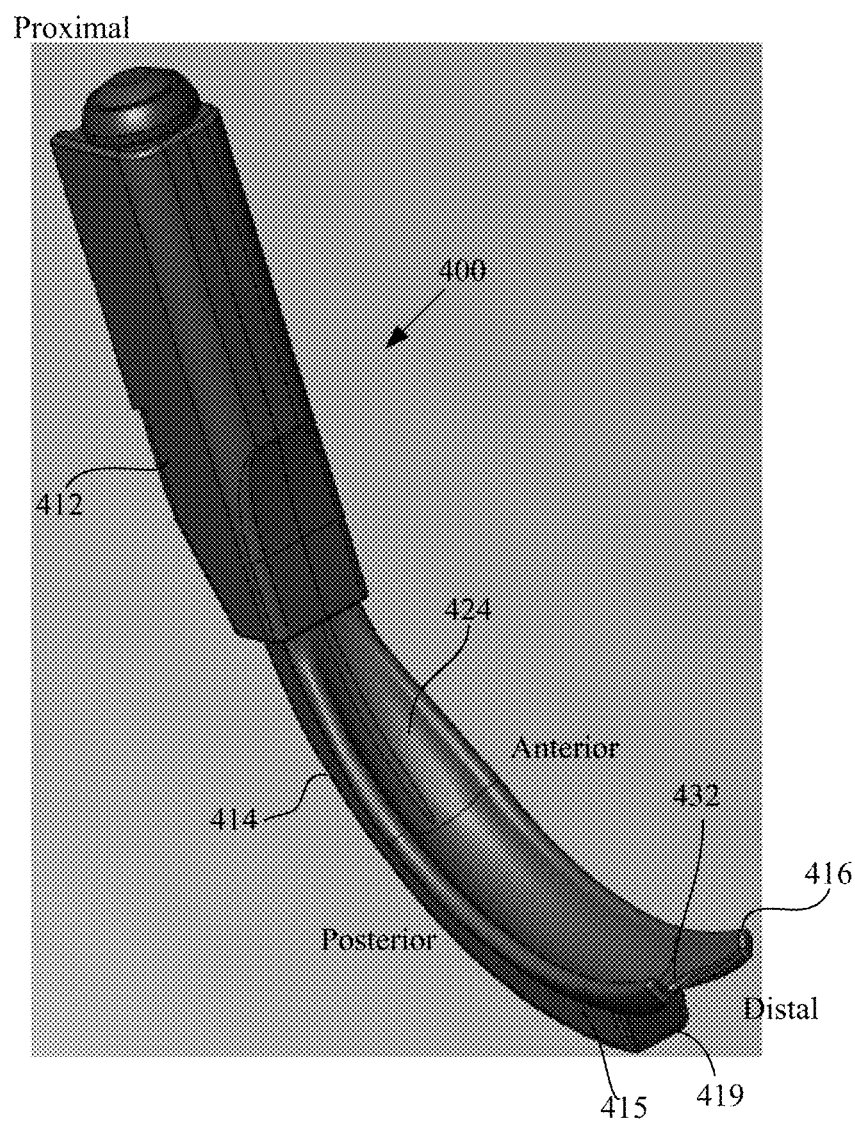
FIG. 21 depicts a side perspective view of an alternate embodiment channel laryngoscope 400.

FIG. 21 depicts a side perspective view of an alternate embodiment channel laryngoscope 400. In this embodiment, the anterior disposed external channel 424 begins approximately midway from the proximal end of the handle 412 and continues into the blade 414 to the distal disposed notch 432.

Adjacent bracketing the notch 432 are tube guides 416. Video camera chamber 415 is located beneath or posterior to the external channel 424 and terminates with widow 419 that similarly houses a video camera 47 and light source 45 (not shown).

FIGS. 22A-D depict side, front, and top views of the channel laryngoscope 400, shown with reference to FIG. 21 shown fitted with a sheath 500.

Figure 22A:
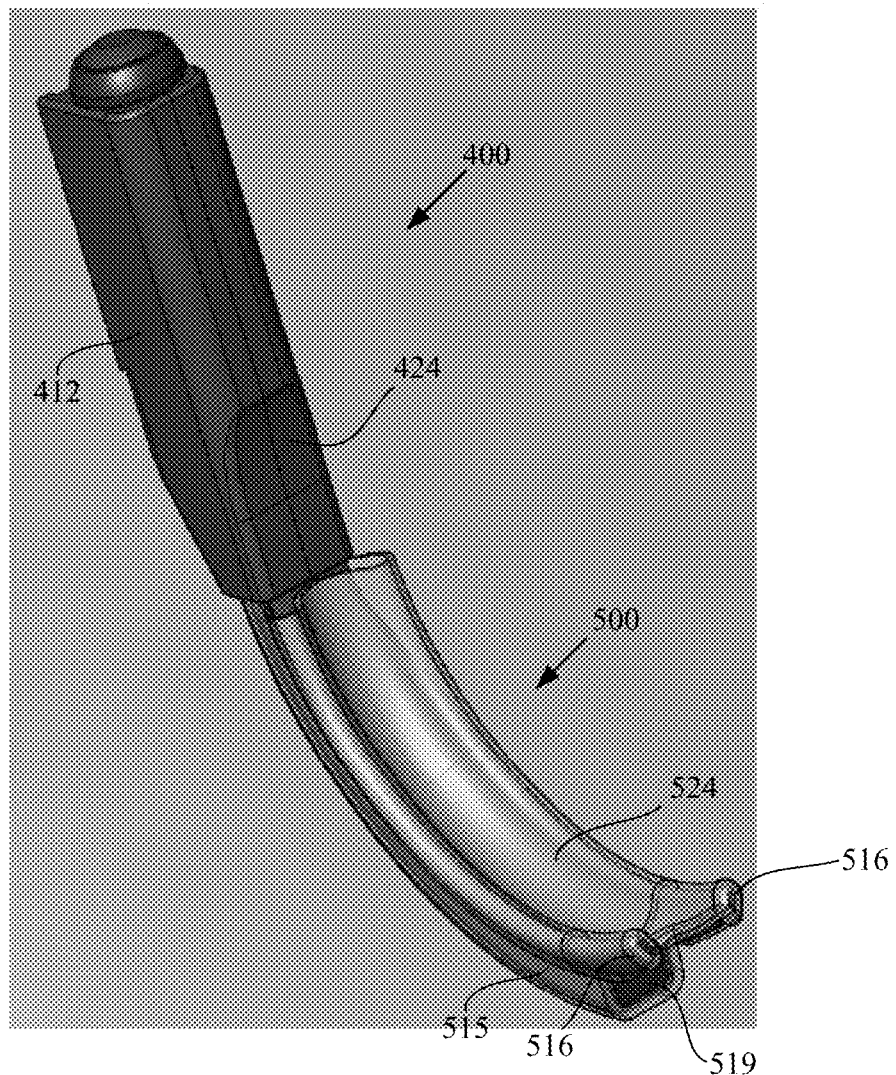
FIG. 22A-D depict side, front, and top views of the channel laryngoscope 400 fitted with the sheath adapter 500.

FIG. 22A depicts a side perspective view of a hard shell sheath 500 adapted to be detachably affixable to the blade 414 of the channel laryngoscope 400 shown in FIG. 21. The sheath 500 is comparatively shaped and slightly larger than the laryngoscope's 400 blade 414. The sheath 500 is slidably affixable to the blade 414 and can readily detach. The sheath 500 includes a channel 524 that is substantially continuous with the curvature of the channel 424 of the handle 412. Sheath video chamber cover 515 overlaps video chamber 415. Similarly, window 519 covers laryngoscope window 419 and sheath tube guides 515 fit over the laryngoscope tube guides 416.

Figure 22B:
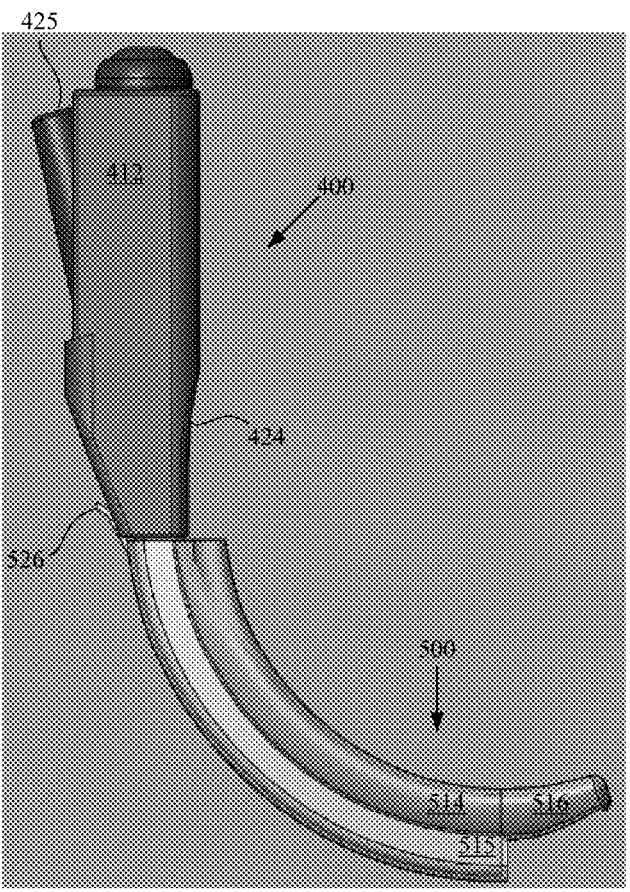

FIG. 22B depicts a side view of the channel laryngoscope 400 fitted with the sheath 500. The sheath 500 is secured to the handle 412 of laryngoscope 400 via snap clasp 526. Video access port 425 allows for insertion and removal of a video camera and lighting units.

Figure 22C:
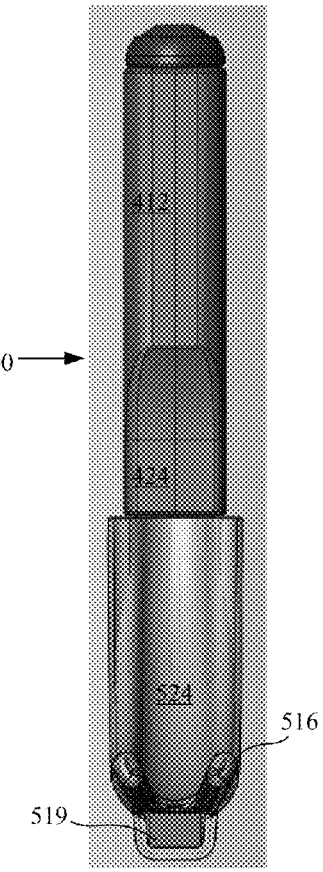
Figure 22D:
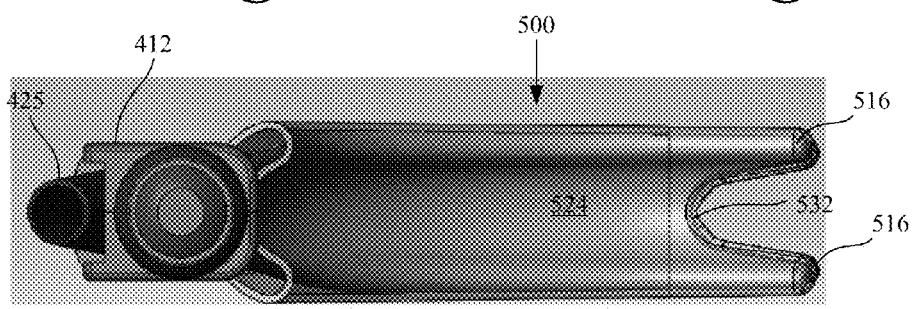

FIG. 22C front view illustrates the continuous pathway afforded by the sheath channel 524 with handle's 412 channel 424.

FIG. 22D top view illustrates the access port 425 in relation to the handle 412 and its co-linear disposition to the sheath's channel 524. Sheath notch 532 is shown in the middle of the tube guides 516.

FIGS. 23A-E depicts side, front, and top views of the channel laryngoscope 600 fitted having a spatula 640 at its distal end.

Figure 23A:
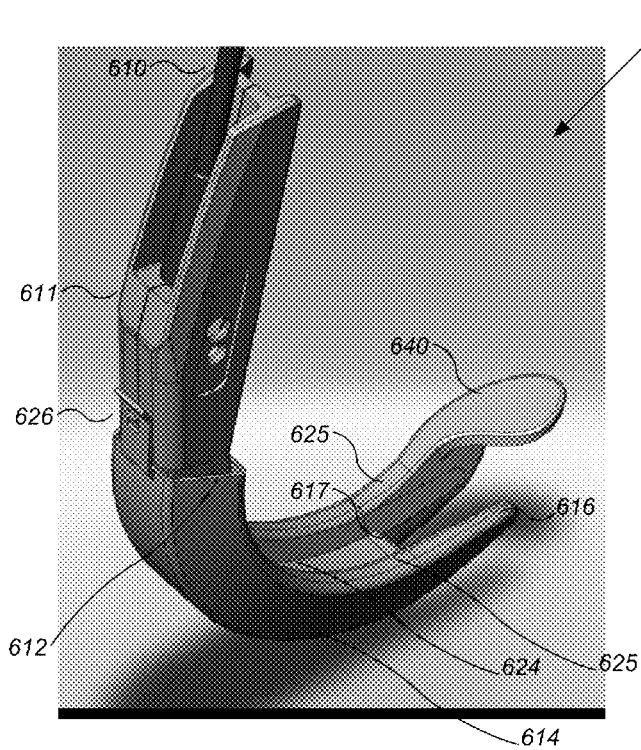
FIGS. 23A-E depicts side, front, and top views of the channel laryngoscope 600 fitted having a spatula 640 at its distal end.

FIG. 23A depicts a side perspective view of a sheath 612 adapted to be detachably affixable to inserted video wand 611 of the channel laryngoscope 600. The sheath 612 defines an internal chamber (not shown) that is comparatively shaped and slightly larger than the insertable portion of the video baton and/or video wand 611. The sheath 614 is slidably affixable to the wand 611 and can readily detach. The sheath 612 includes a channel 624 that is substantially continuous with the curvature of the channel of the wand 611. The channel 624 is bracketed by two continuous ridges 625 that follow the curvature of the sheath 612. The sheath 612 is secured to the wand 611 of laryngoscope 600 via snap clasp 626. The wand 611 provides a connection to a power and communications cord 610. The channel 624 terminates near the distal end of the sheath 617 and tube guides 616 extend continuously from the ridges 625. The tube guides 616 define an opening between themselves and the terminus 617 of the channel 624 that enables the passage of an endotracheal tube. The sheath includes a generally flat disc shaped spatula 640 that is coupled to an anterior portion of a tube guide 616 and generally extends in a parallel plane to the plane that is defined by the channel 624. The spatula 640 extends into the space between the tube guides 616. As described above, the tube guides 616 are configured to displace the epiglottis. The spatula 640 is also configured for displacing the epiglottis. In an embodiment, the spatula 640 may extend from the sheath 612 such that the plane defined by the spatula 640 forms an angle with the plane defined by the channel 624. Similarly the tube guide 616 may extend from the sheath 612 such that the plane defined by the tube guide 616 forms an angle with the plane defined by the channel 624. The plane defined by the spatula 640 may be parallel to the plane defined by tube guide 616 or may form an angle with respect to it.

Figure 23B:
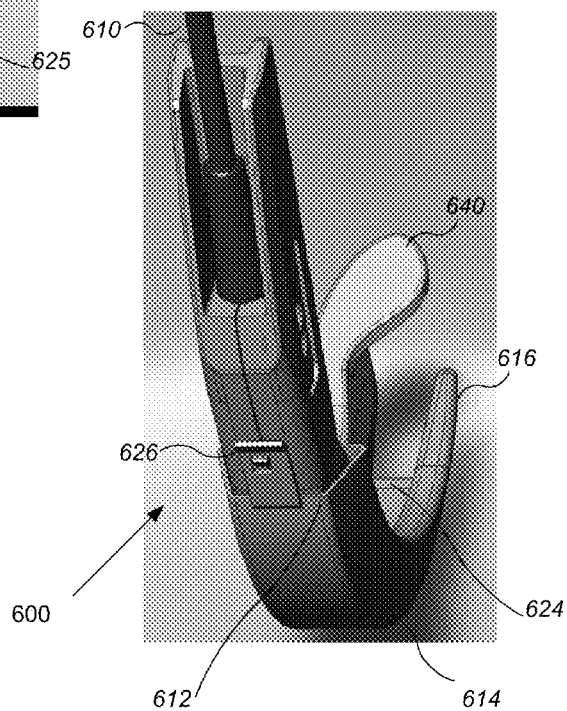

FIG. 23B depicts a rear view of the channel laryngoscope 600 fitted with the sheath 612. The sheath 612 is secured to the handle 611 of laryngoscope 600 via snap clasp 626.

Figure 23C:
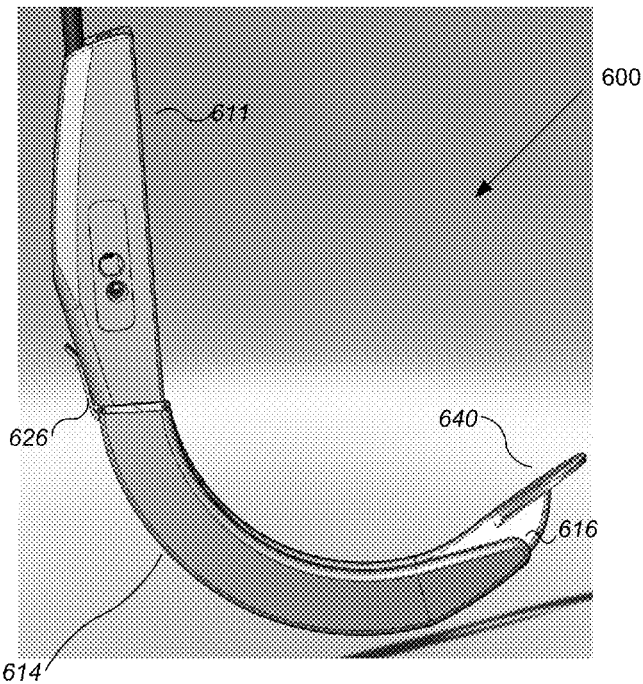

FIG. 23C side view illustrates the spatula 640 and its relationship with the tube guide 616. In this embodiment the plane defined by the spatula 640 defines an angle with respect to the plane defined by the tube guide 616.

Figure 23D:
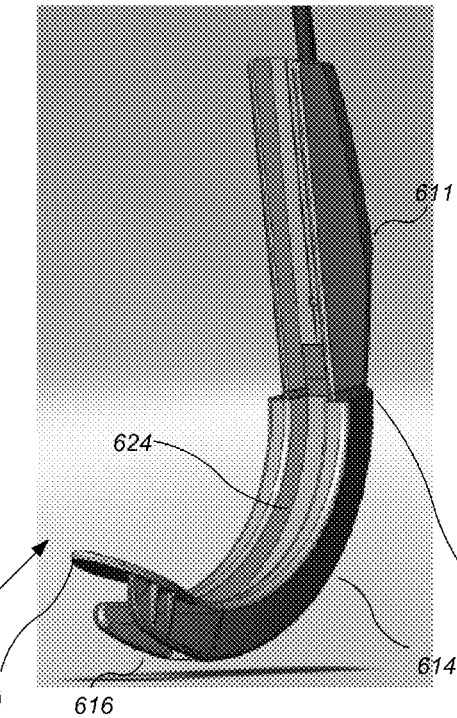

FIG. 23D front view illustrates the continuous channel 624 through the handle 611 and the sheath 612. The channel terminates at tube guides 616, a spatula 640 extends outwardly from the tube guides. In an embodiment, the laryngoscope has a single tube guide 616 and a spatula 640. The spatula 640 is attached to the sheath 612 and is a flat surface that extends inwardly toward the channel 624.

Figure 23E:
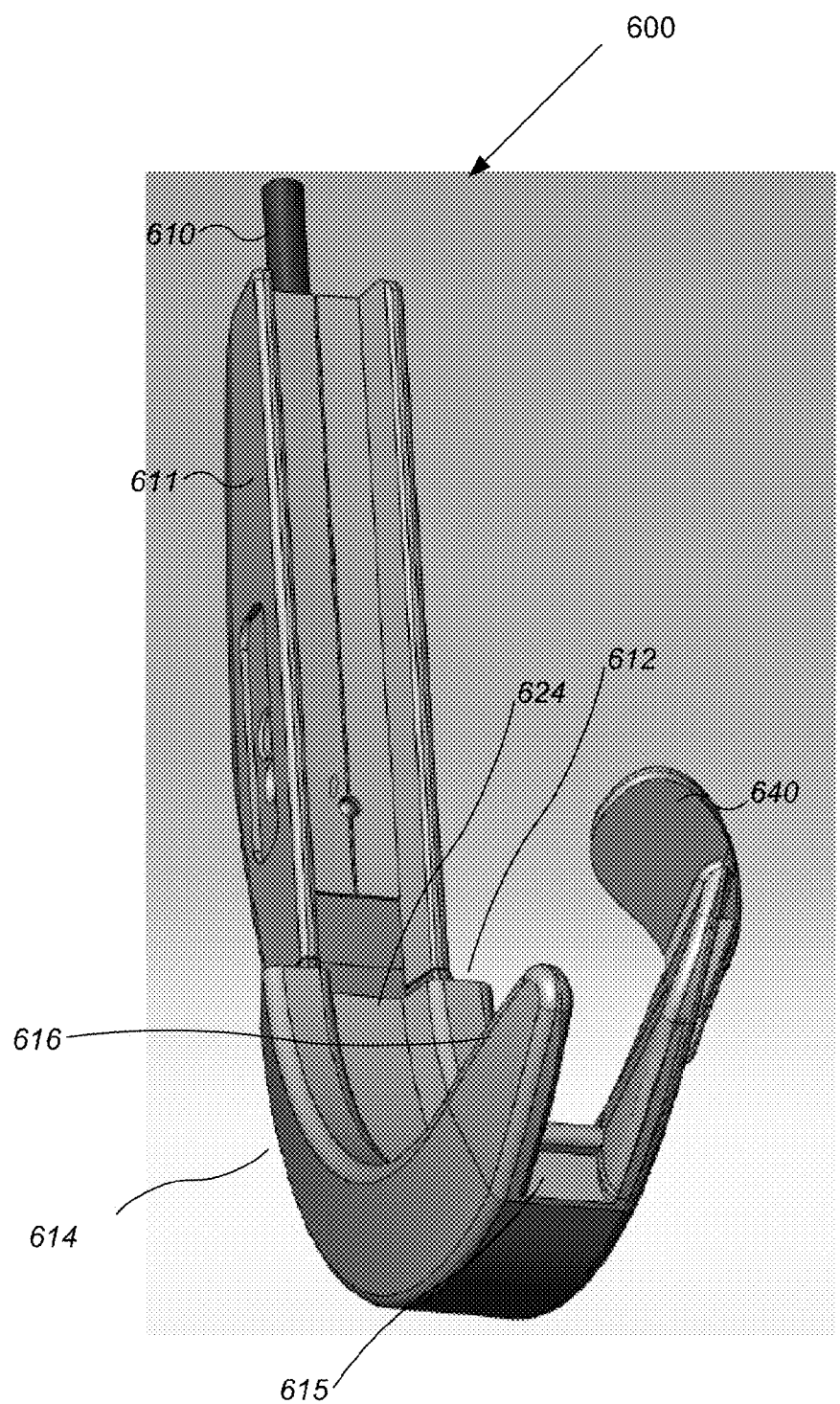

FIG. 23E front view illustrates a sheath 612 with video chamber cover 615 that covers an inserted camera (not shown).

Figure 24:
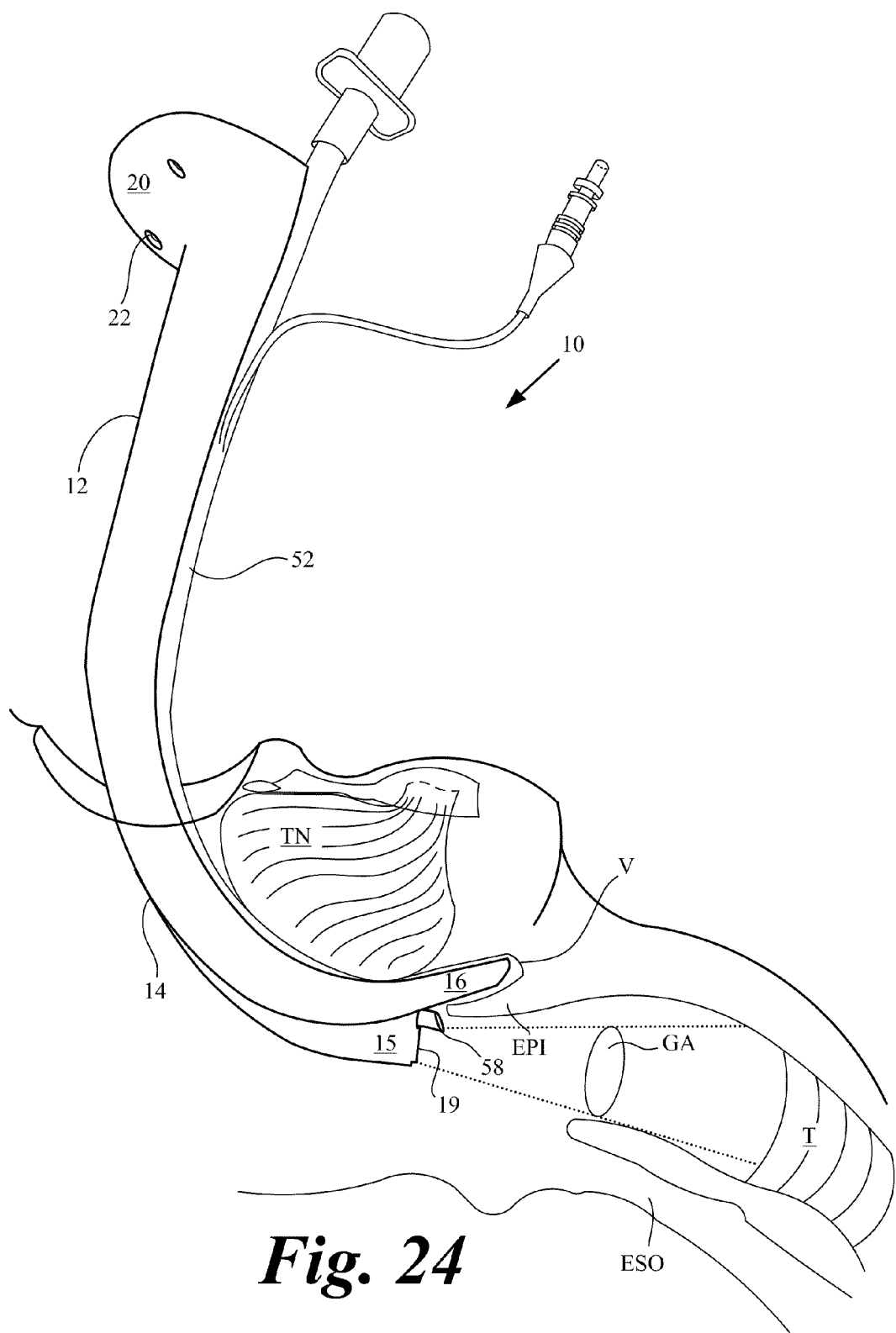
FIG. 24 depicts the movement of a patient's epiglottis EPI away from the glottic aperture GA by engagement of the vallecula V with either or both of the tips of the tube guides 16 of laryngoscope 10.

FIG. 24 depicts the movement of a patient's epiglottis EPI away from the glottic aperture GA by engagement of the vallecula V with either or both of the tips of the tube guides 16 of laryngoscope 10. The epiglottis EPI normally obscures the glottic aperture GA and acts as a barrier to passage of an ETT. Pressing the tip or tips of the tube guide or guides 16 of the laryngoscope 10 into the vallecula V tenses the hyo-epiglottic ligament (not shown) to pull the epiglottis upwards and expose the glottic aperture GA for passage of the intubation 52. Shown is a light beam (dotted lines) from the light source 45 behind window 19 which illuminates the glottic aperture GA and immediate surroundings, including the trachea T. The ETT 52 is in contact with the patient's tongue TN and tube aperture 58 extends slightly from notch 32 and has a trajectory lined up for entry into and through the glottic aperture GA to the trachea T. The esophagus ESO is seen beneath the trachea T. Pressing the vallecella V to swing open the epiglottis EPI can also be achieved by distal tip or tips of tube guides 116, 316, 416, and 516 of the laryngoscope/sheath embodiments 100, 300, 400, and 500.

Figure 25:
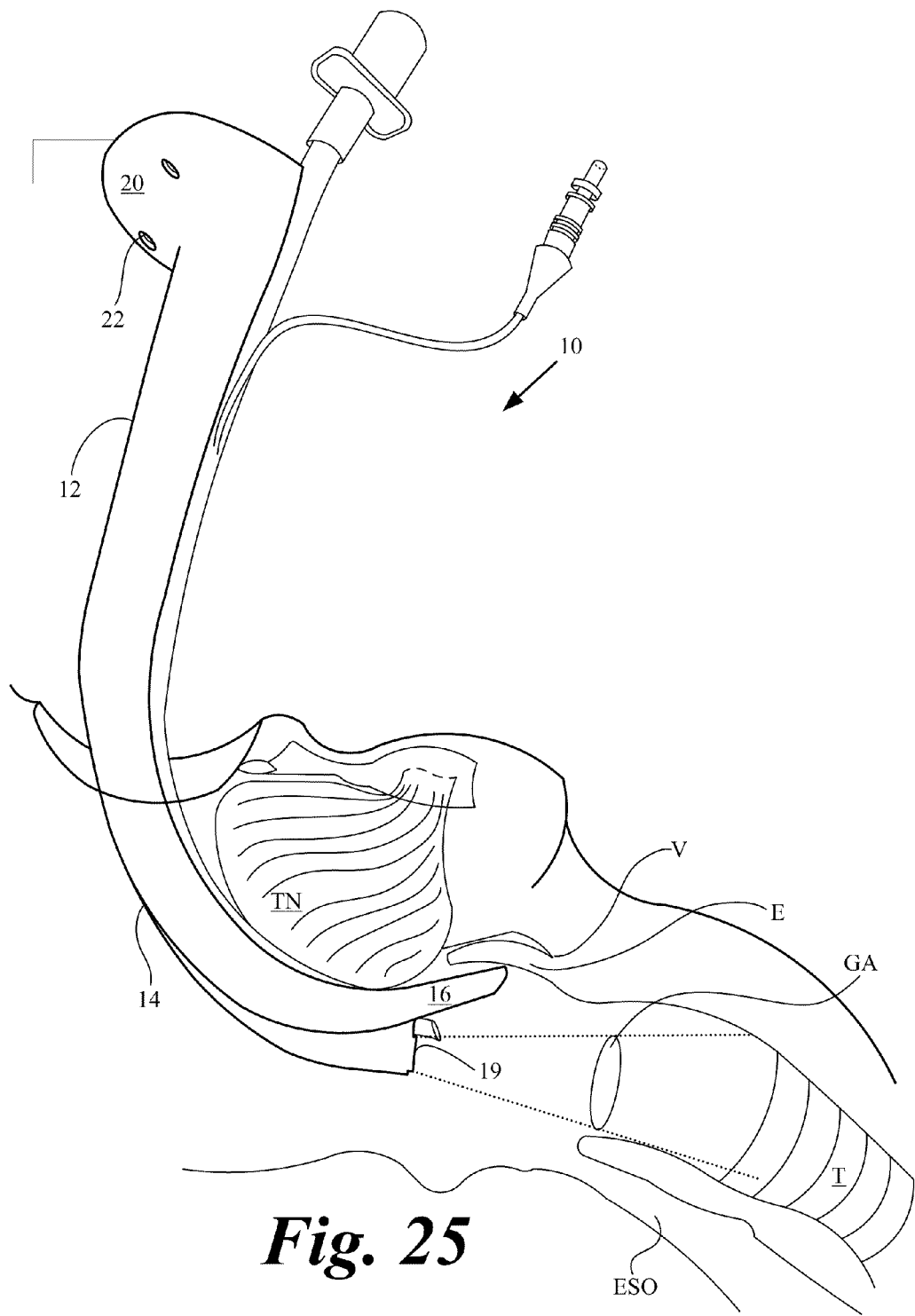
FIG. 25 depicts the movement of a patient's epiglottis EPI away from the glottic aperture GA by lifting the epiglottis EPI by either or both of the tips of the tube guides 16 of laryngoscope 10.

FIG. 25 depicts the movement of a patient's epiglottis EPI away from the glottic aperture GA by lifting the epiglottis EPI by either or both of the tips of the tube guides 16 of laryngoscope 10. Shown is a light beam (dotted lines) from the light source 46 behind window 19 and clearly illuminates the glottic aperture GA now revealed by the direct lifting of the epiglottis EPI. Tube aperture 58 of the ETT 52 is shown with a trajectory lined passage through the glottic aperture GA and into the trachea T. Direct lifting of the epiglottis EPI can also be achieved by the distal tip or tips of tube guides 116, 316, 416, and 516 of the laryngoscope/sheath embodiments 100, 300, 400, and 500.

Figure 26:
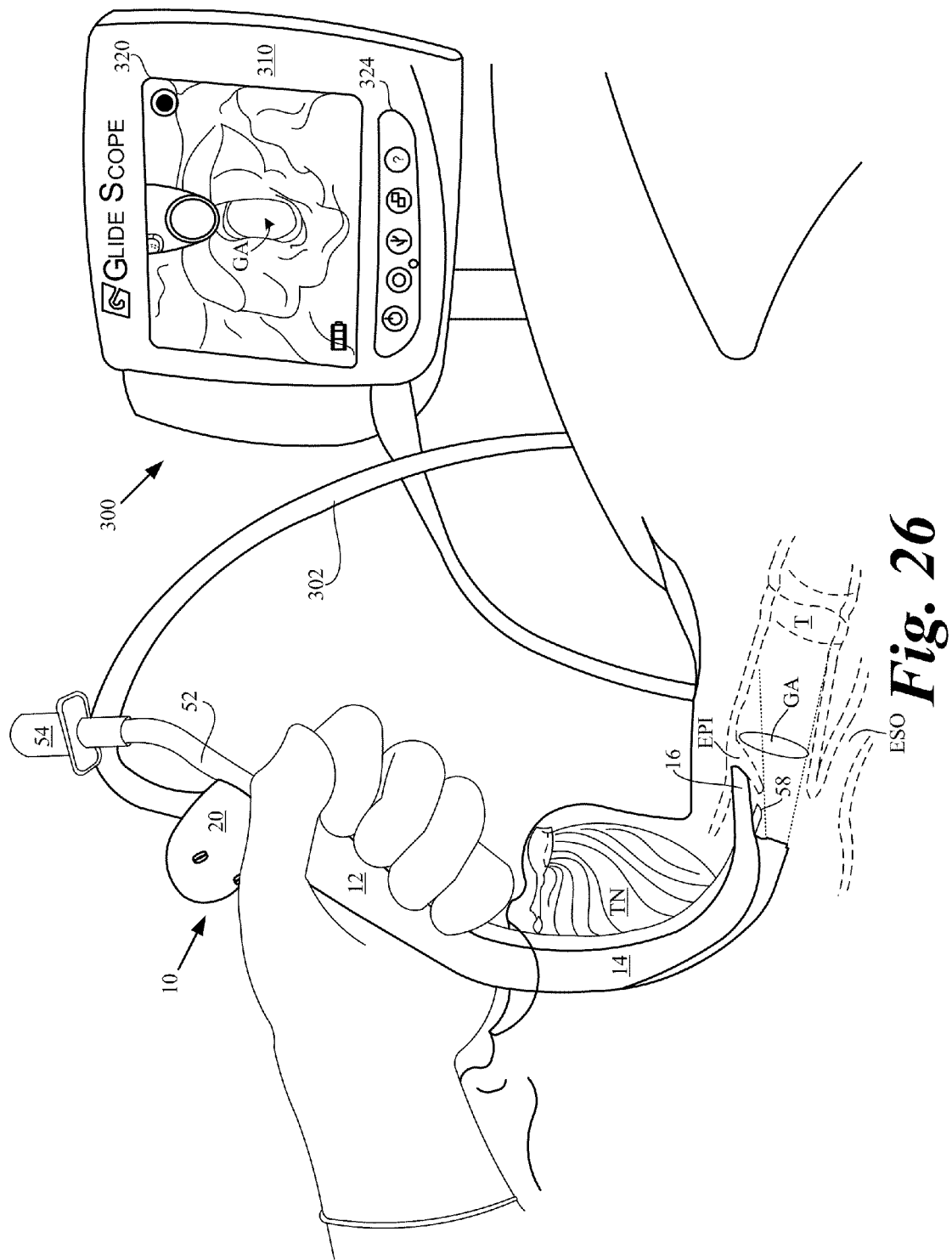
FIG. 26 depicts a video laryngoscope system 300 using the channel laryngoscope 10 loaded with an ETT 52 during intubation of a patient using engagement of the vallecula V to swing open the epiglottis EPI depicted in FIG. 24.

FIG. 26 depicts a video laryngoscope system 300 using the channel laryngoscope 10 loaded with an ETT 52 during intubation of a patient using engagement of the vallecula V to swing open the epiglottis EPI depicted in FIG. 24. The cable 302 connects the channel laryngoscope 10 cable connector 42 to a monitor 310 having a display 320 and a display control panel 324. The monitor 310 is constructed of MRI compatible materials. Images from the video camera 48 are conveyed to present a view of the patient's trachea T on the display 320. The channel laryngoscope 10 may be pre-loaded with the ETT 52 such that its terminal opening 58 is placed between the guides 16 near the notch 32. The ETT loaded channel laryngoscope 10 may be placed midline into the patient's oropharynx and obtain a user desired glottic view of the trachea T by slightly advancing, retracting, and/or tilting the channel laryngoscope 10 as needed. The trachea T may generally be placed in the middle to upper third of the display 320 by the user manipulating the position of the channel laryngoscope 10 within the oropharynx.

Alternate embodiments of the video laryngoscope system 300 may include the channel laryngoscope 10 fitted with sheath adapter 100 in which the ETT 52 or tube 72 may be positioned as for intubation delivery. Similarly, another alternate embodiment of the video laryngoscope system 300 may include the channel sheath 200 embodiment with removable video wand 270 to be employed with ETT.

Figure 27:
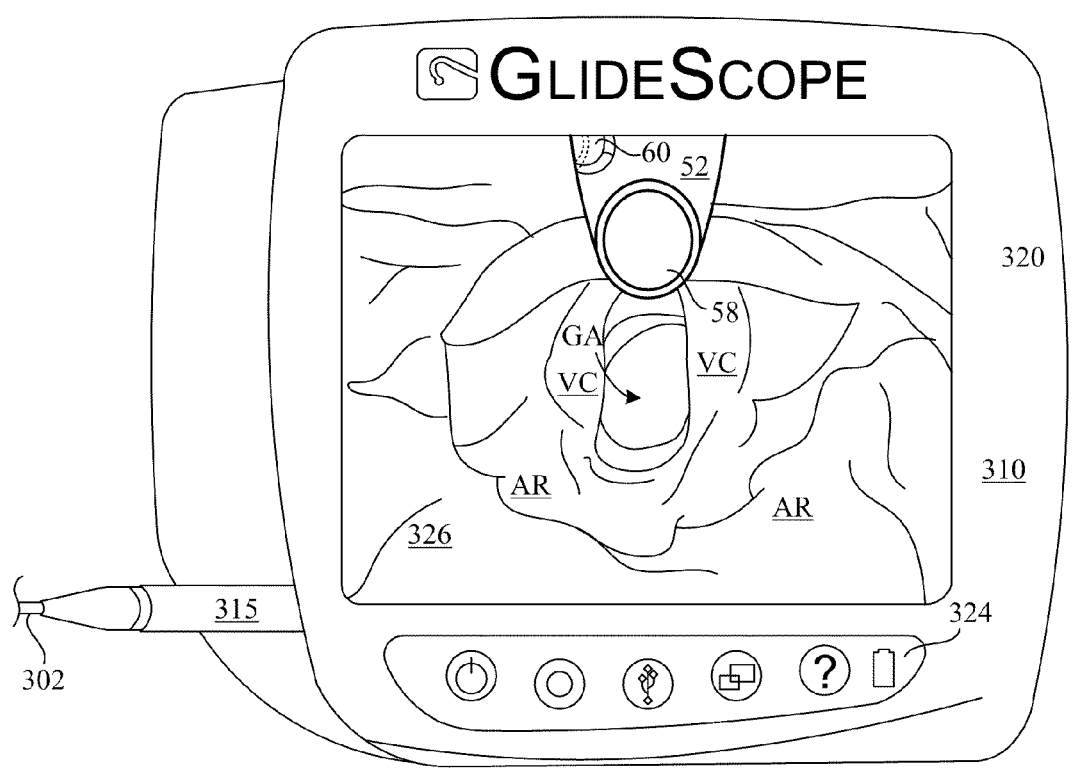
FIG. 27 depicts a first monitor view 326 obtained from the channel laryngoscope 10 of a patient's trachea during centering of the ETT prior to intubation.

FIG. 27 depicts a first monitor view 326 obtained from the channel laryngoscope 10 engagement of the vallecula V to swing open the epiglottis EPI depicted in FIG. 24 to expose a patient's glottic aperture during centering of the ETT prior to intubation. Here, first monitor view 326 shows the ETT terminal opening 58 center aligned above the patient's glottic aperture GA. A portion of the side aperture 60 of ETT 52 is in the upper field of view as presented in display 320 of monitor 310. Vocal cords VC and arytenoids AR are shown.

Figure 28:
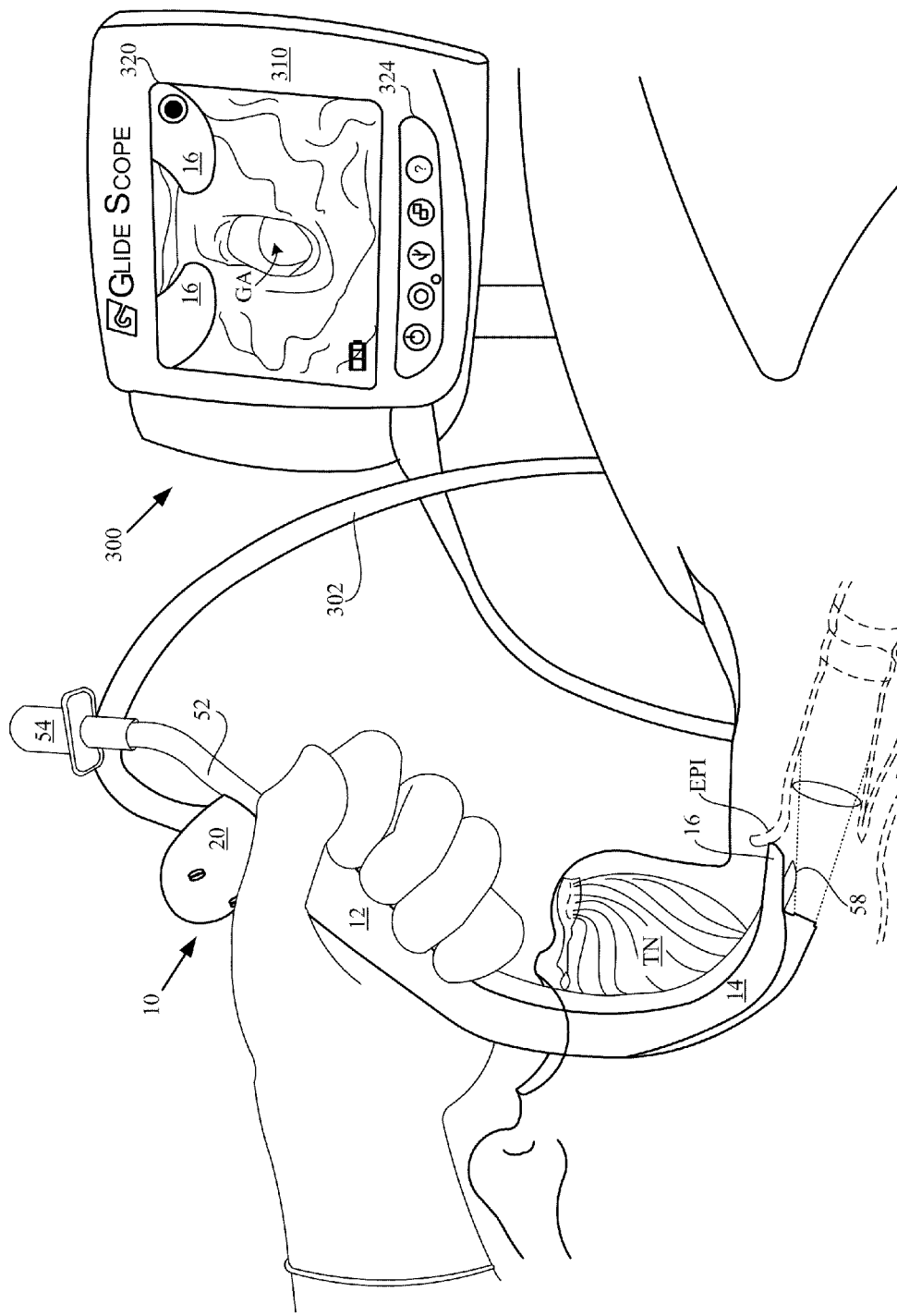
FIG. 28 depicts the video laryngoscope system 300 using the channel laryngoscope 10 loaded with an ETT 52 during intubation of a patient using direct lifting of the epiglottis EPI depicted in FIG. 25.

FIG. 28 depicts the video laryngoscope system 300 using the channel laryngoscope 10 loaded with an ETT 52 during intubation of a patient using direct lifting of the epiglottis EPI depicted in FIG. 25. The cable 302 connects the channel laryngoscope 10 having cable connector 42 to a monitor 310 having a display 320 and a display control panel 324. The monitor 310 is constructed of MRI compatible materials. Images from the video camera 48 are conveyed to present a view of the patient's trachea T on the display 320. The channel laryngoscope 10 may be pre-loaded with the ETT 52 such that its terminal opening 58 is placed between the guides 16 near the notch 32. The ETT loaded channel laryngoscope 10 may be placed midline into the patient's oropharynx and obtain a user desired glottic view of the trachea T by slightly advancing, retracting, and/or tilting the channel laryngoscope 10 as needed. The trachea T may generally be placed in the middle to upper third of the display 320 by the user manipulating the position of the channel laryngoscope 10 within the oropharynx.

Figure 29:
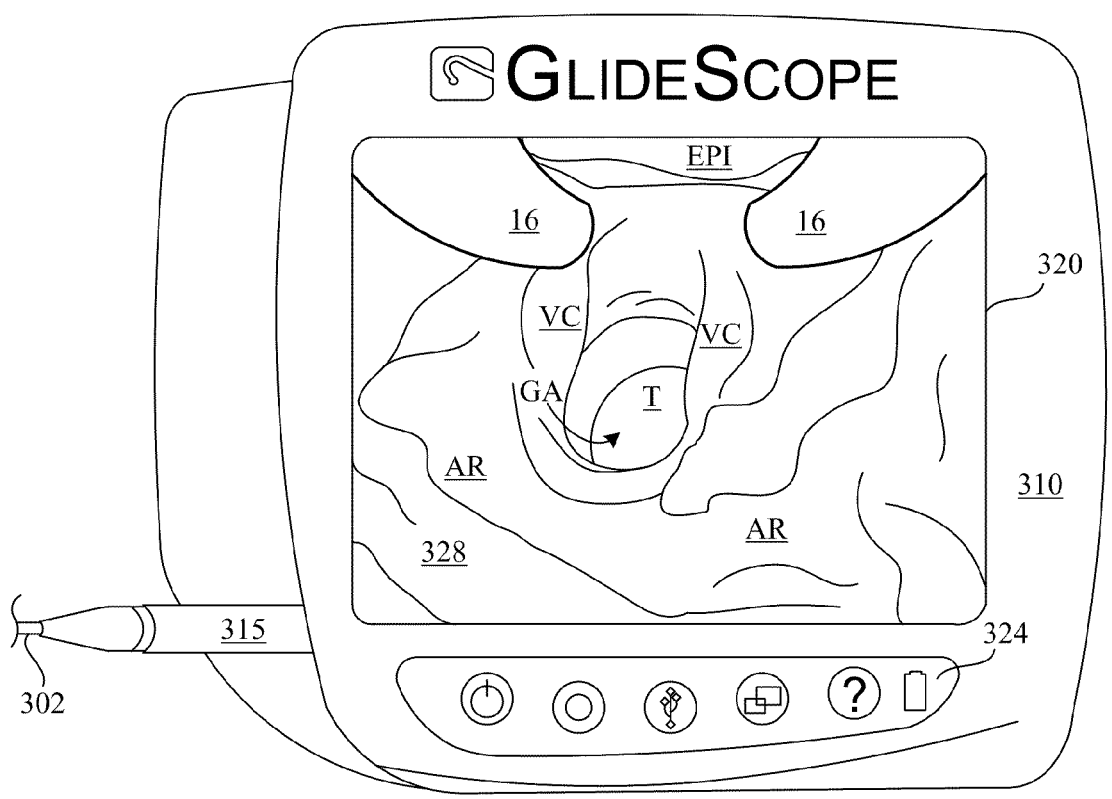
FIG. 29 depicts a second monitor view 328 obtained from the channel laryngoscope 10 of the patient's trachea T during intubation of the centered ETT 52.

FIG. 29 depicts a second monitor view 328 obtained from the channel laryngoscope 10 engagement via direct lifting of the patient's epiglottis EPI by tube guides 16 depicted in FIG. 25 to expose the patient's glottic aperture. Here the tube guides 16 are captured in monitor view 328 and shown holding the epiglottis EPI and revealing the glottic aperture GA for intubation by pushing the ETT (not in camera's 47 field of view distally towards the glottic aperture GA for placement within the trachea T. The user may continue to the push the ETT 52 further into the trachea T to pass the inflatable cuff 64 for placement therein. Nearby vocal cords VC and arytenoids AR are seen.

In other embodiments the camera 47 may have different telescopic views in which the channel or tube guides 16 are not visible in the monitor images, but only the ETT's 52 end aperture 58 and/or side aperture 60 are visible. In this instance, the tube end 58 can be used as its own aiming guide for the user to make laryngoscope positional adjustments with the patient's oropharynx to align delivery of the ETT end 58 into the trachea T aperture.

Figure 30:
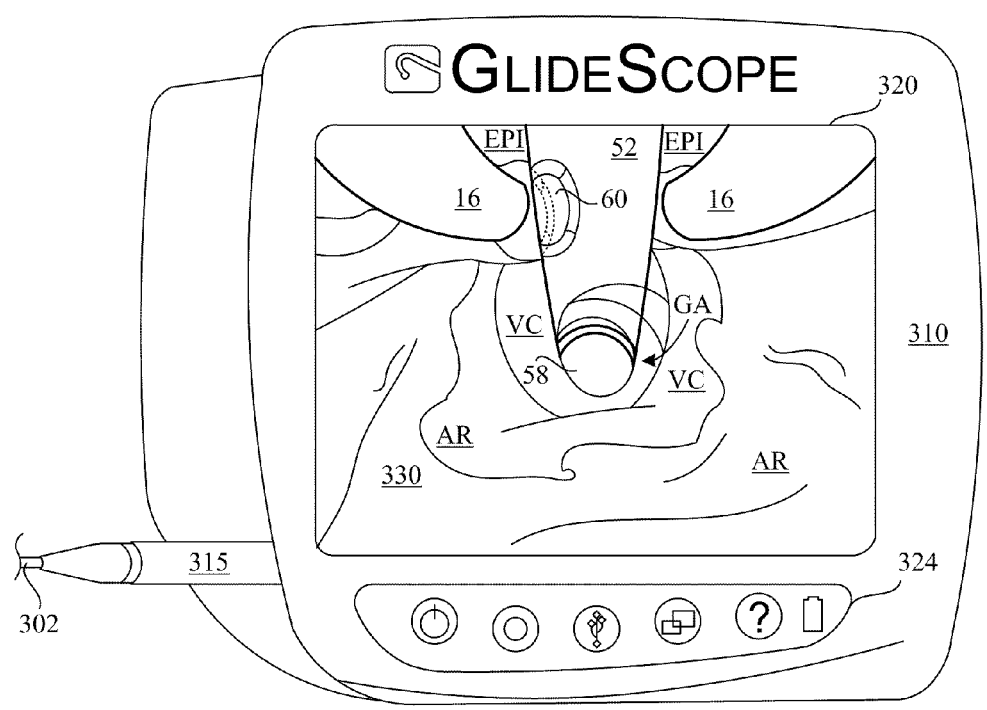
FIG. 30 depicts a third monitor view 330 obtained from the channel laryngoscope 10 of the patient's trachea T during intubation of the centered ETT 52.

FIG. 30 depicts a third monitor view 330 obtained from the channel laryngoscope 10 during intubation through the glottic aperture GA while the patient's epiglottis EPI is directly lifted and held by laryngoscope 10 tube guides 16. The Murphy's Eye 60 is seen progressing toward the glottic aperture GA and terminal aperture 58 of ETT 52 is shown passing beyond the glottic aperture GA. The user may continue to the push the ETT 52 further into the trachea T to pass the inflatable cuff 64 beyond the glottic aperture GA.

Figure 31:
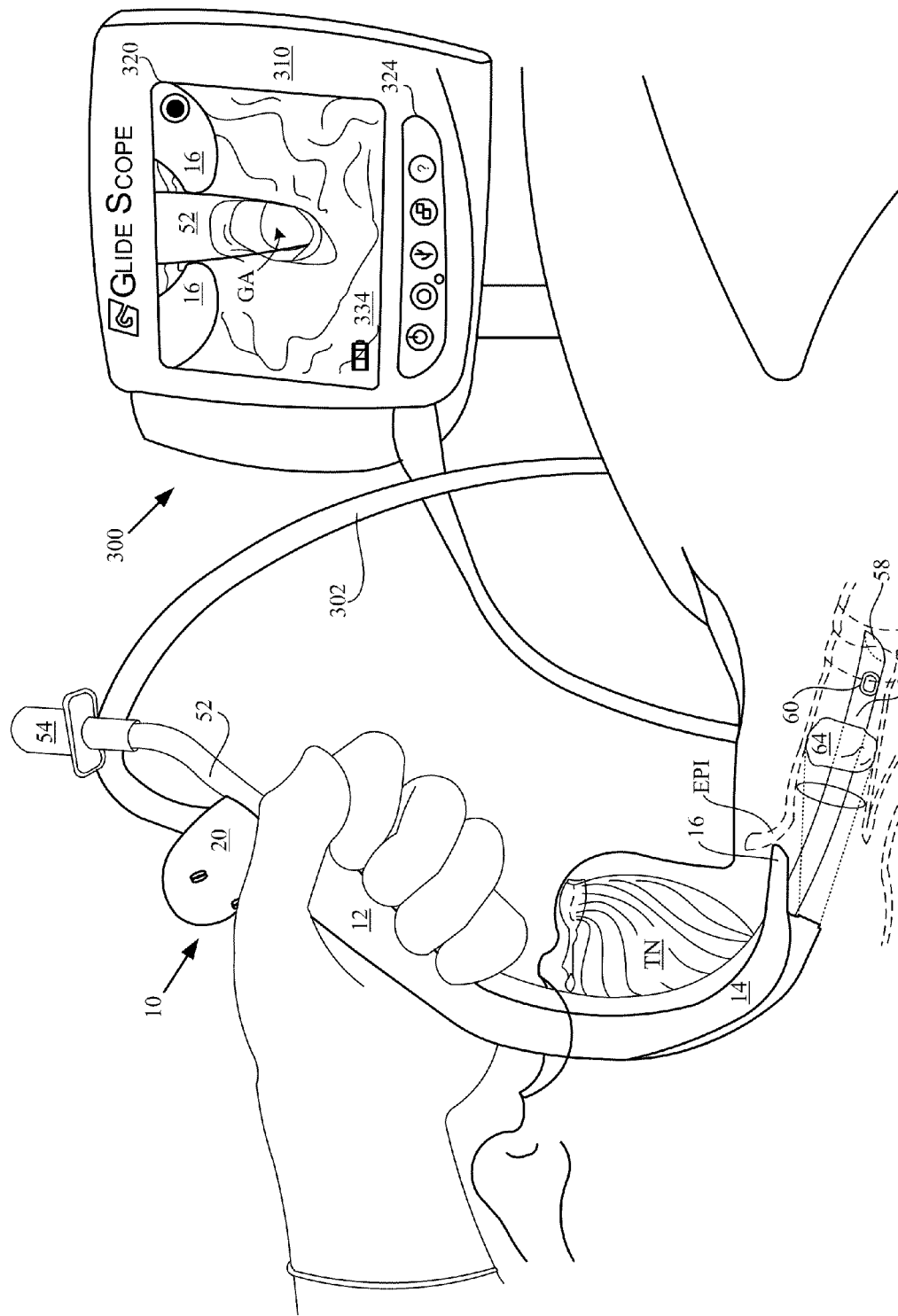
FIG. 31 depicts placement of the ETT 52 within the trachea T while maintaining direct lifting of the epiglottis EPI.

FIG. 31 depicts placement of the ETT 52 within the trachea T while maintaining direct lifting of the epiglottis EPI depicted in FIGS. 28 and 30. Inflatable cuff 64 is shown internally passed beyond glottic aperture GA and inflated against the tracheal walls to secure the ETT 52 within the trachea T. Image 334 on monitor 310 shows the ETT 52 having penetrated the glottic aperture GA with the terminal aperture 58 and Murphy's Eye 60 absent from image 334.

The video laryngoscopes secured into the transparent or non-transparent disposable sheaths may be inserted into the patient's mouth to provide clear camera viewing through the optically clear ports of the transparent or non-transparent disposable sheaths to allow endotracheal procedures to be undertaken. The transparent or non-transparent disposable sheaths may be used just once for a given patient. Video laryngoscopes in the form of a baton are configured to be detachably removable from the disposable sheath removed from a patient and re-inserted into another sterilized disposable sheath for insertion into another patient. The reusable video laryngoscope batons may then undergo high-level disinfection after a series of clinical exams have been completed.

Other embodiments described encompass reusable video laryngoscopes having flexible cameras that are insertable into transparent or non-transparent disposable sheaths having clear optically clear viewing windows that receive contact with camera. The reusable video laryngoscopes are configured to be detachably secured by locking tabs located in the transparent or non-transparent disposable sheaths with complementary shaped posts and ledges of the video laryngoscopes. The video laryngoscopes that are secured into the transparent or non-transparent disposable sheaths may be inserted into the patient's mouth to provide clear camera viewing through the optically clear window ports of the transparent or non-transparent disposable sheaths to allow endotracheal procedures to be undertaken. The transparent or non-transparent disposable sheaths are sterilizable and may be used just once for a given patient. Video laryngoscopes in the form of a baton are configured to be detachably removable from the disposable sheaths and removed from a patient and re-inserted into another sterilized disposable sheath for insertion into another patient. The reusable video laryngoscope batons may then undergo high-level disinfection after a series of clinical exams have been completed.

Other embodiments described herein include a video laryngoscope system having a video laryngoscope having a handle and a flexible camera and a transparent sheath having a tongue blade with an optically clear window, a chamber configured to receive the handle and the flexible camera, and a locking tab configured to engage at least one surface of the laryngoscope handle. The configuration provides for insertion of video laryngoscope into the chamber of the sheath or stat such that the video laryngoscope fits into the chamber with the locking tab to attachably engage with the at least one surface to slidably bring the camera in contact with the optically clear window. Other embodiments provide for the at least one locking tab to include adjoining tapered wedges that are engageable with the surface of the at least one surface of the laryngoscope handle. Video laryngoscopes in the form of a baton are detachably removable from the disposable sheath exposed to a patient and can be readily inserted into another sterile disposable sheath for application to a different patient.

Cameras 47 of the non-removable or removable video batons may include CCD or CMOS configurations that may be placed having a clear perspective view over the notch 32 between the tube guides 16 extending from blade 14. The camera may be similarly configured to have optimal clear views of the notches 132 and 532 of the sheaths 100 and 500.

The camera may be placed near the midpoint of the blade 14 to provide for distance from the glottic aperture to allow a degree of perspective, wide angle, and/or telescoping viewing. The position of the camera may be readjusted by disengaging the video wand or baton's handle locking pins, ridges, or ledges from the sheath's locking tabs to provide for the camera to be withdrawn slightly from the sheath's clear viewing ports.

Other embodiments of the video based laryngoscopes can be used beyond direct laryngoscopic examination and intubation. The video-based laryngoscopes 10, 100, and 200 may be adapted for indirect laryngoscopic procedures. For example, if a user is comfortable with using an ETT tube loaded stylet instrument, the video-based laryngoscopes 10, 100, and 200 may serve as observational platforms to provide "live" images to the monitor 310 display screen 320 so that indirect laryngoscope intubation procedures utilizing mirror-based devices can be performed.

The system 300 can be employed for endotracheal intubation, laser-based surgical and biopsy procedures, and passage of ancillary equipment. Algorithms described below employ the channel laryngoscope 10, but may be suitably adapted to employ channel laryngoscopes and laryngoscope sheaths 100, 200, 400, and 500. The indirect intubation procedures can be adapted to place single or double lumen tubes, or to remove a foreign body. Other indirect laryngoscope procedures include directing a flexible laryngoscope, a Bougie, or a bronchoscope and to guide ears-nose-throat (ENT) personnel operating a jet ventilator to perform biopsy and/or laser treatments to the patient.

The algorithms can be employed to enable the passage and control of a number of tools useful for surgery and procedures in and around the airway such as simultaneous visualization and conduct of surgical laser operating systems, electro-surgical operating wands, surgical biopsy instruments, surgical suction devices, jet ventilation systems for transglottic ventilation during laryngeal and airway surgery, double lumen endotracheal tubes commonly used for lung separation during surgical procedures on the thoracic structures, flexible bronchoscopes and gastroscopes, Transesophageal Echo probes, and nasogastric tubes. FIGS. 32-35 below describe representative algorithms for the devices usable in the system 300.

Figure 32:
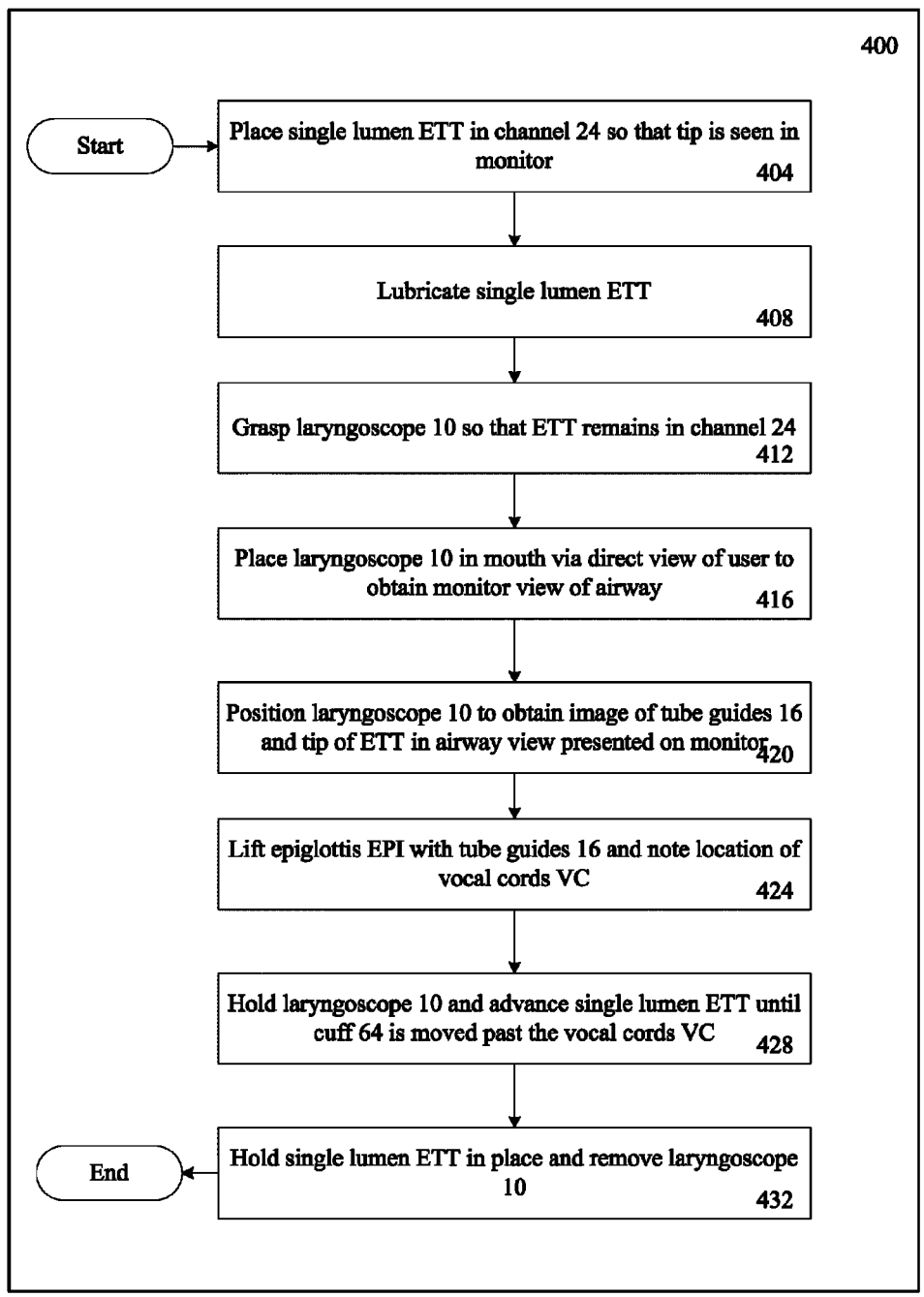
FIGS. 32-35 depict algorithm flow charts utilizing the system 300 depicted in FIGS. 26-31.

FIG. 32 depicts an intubation algorithm 400 for endotracheal intubation of a single lumen tube. Beginning at process block 404, a single lumen ETT is selected and placed in the channel laryngoscope's 10 channel 24 such that the tip of the single lumen ETT is visible on the monitor 320. At process block 408, the ETT is lubricated. At process block 412, the handle is gripped by the user to keep the ETT secured within channel 24. Thereafter, at process block 416, channel laryngoscope 10 is placed into the mouth under direct vision of the user. At process block 420, the user exerts slight pressure on the tongue to displace it forward, and glancing at the monitor 320, confirms the visible presence of the tips of the tube guides 16 and the ETT; At process block 424, the epiglottis is lifted by the tube guides 16 to view the airway; At process block 428, the channel laryngoscope 10 is held and the ETT is advanced until the cuff 64 is moved passed the vocal cords VC. Finally, at process block 432, the ETT is held in place and the channel laryngoscope 10 is removed.

Figure 33:
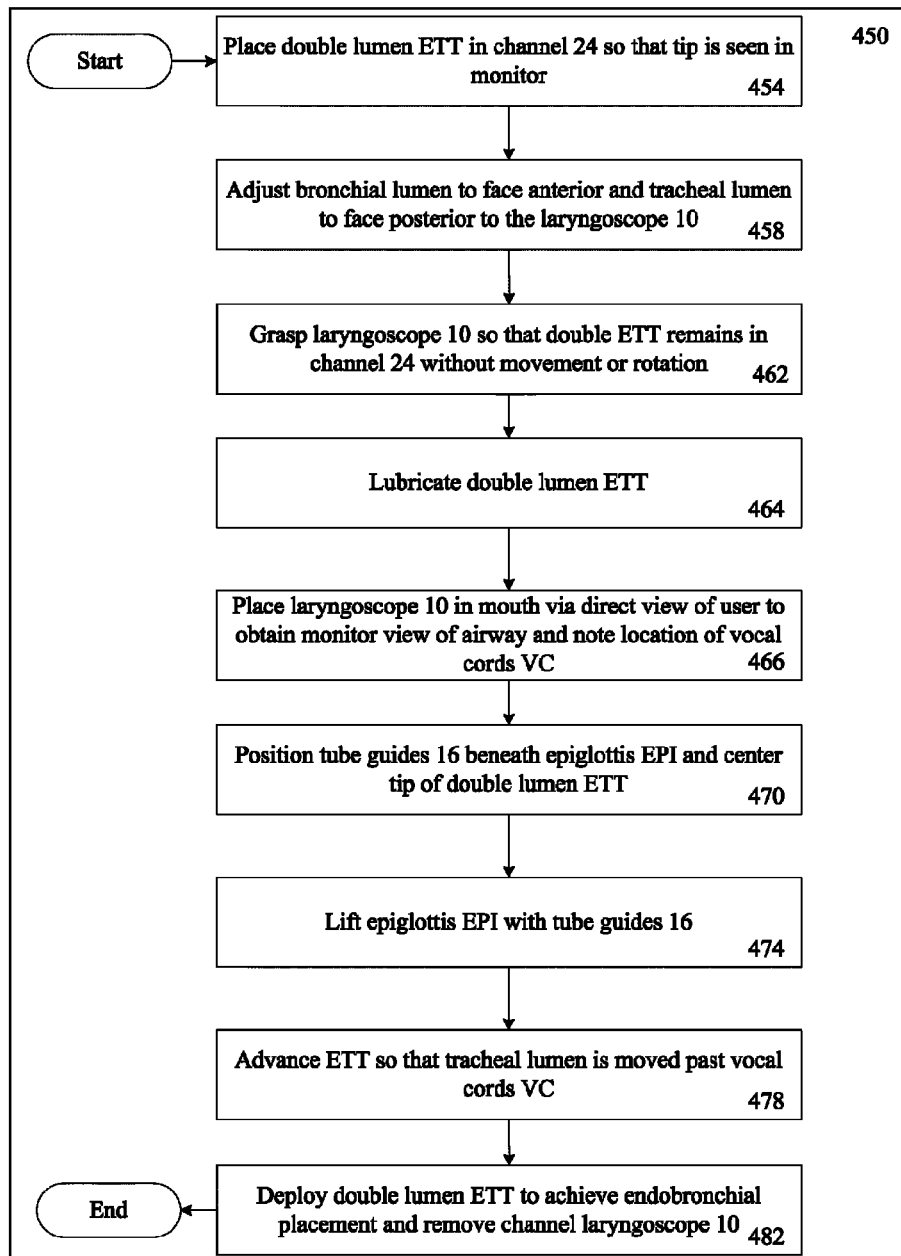

FIG. 33 depicts an intubation algorithm 450 for endotracheal intubation of a double lumen tube. Beginning at process block 454, a double lumen ETT is selected and placed in the channel laryngoscope's 10 channel 24 such that the tip of the double lumen ETT is visible on the monitor 320. At process block 458, the double lumen ETT is adjusted so that the bronchial lumen angles posteriorly and the tracheal lumen faces anteriorly with respect to the laryngoscope 10 position within the patient being intubated. At process block 462, the handle is gripped by the user to keep the double lumen ETT secured within channel 24 in a manner that prevents movement and rotation. Lubricant is applied at process block 464. Thereafter, at process block 466, the channel laryngoscope 10 is placed into the mouth under direct vision of the user and advanced. At process block 470, the user exerts slight pressure on the tongue to displace it forward, and glancing at the monitor 320, confirms the visible presence of the tips of the tube guides 16 and tip of the double lumen ETT. At process block 474, the epiglottis is lifted by the tube guides 16 to view the airway. At process block 478, the channel laryngoscope 10 is held to control the direction of the double lumen ETT transit while the double lumen ETT is advanced until the tracheal lumen is moved passed the vocal cords VC. Finally, at process block 482, the double lumen ETT is deployed to achieve endobronchial placement and the channel laryngoscope 10 is removed.

Figure 34:
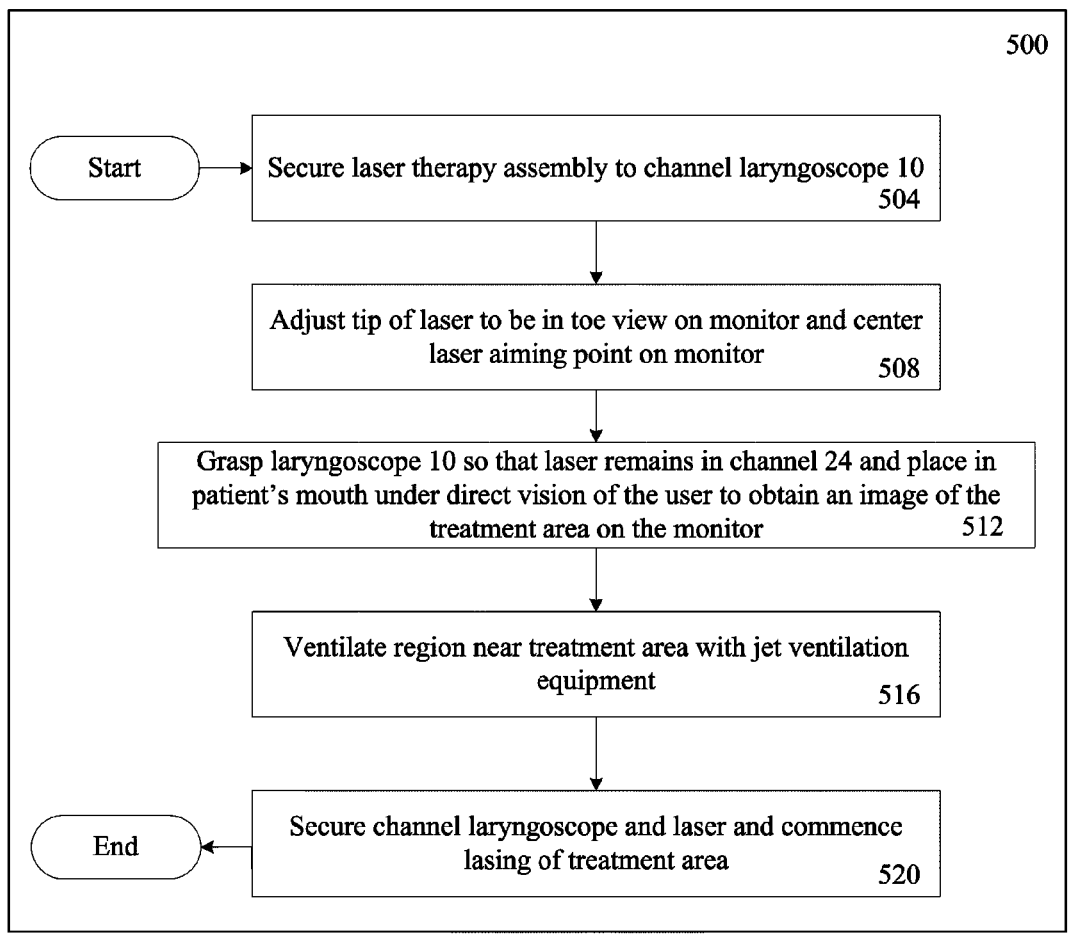

FIG. 34 depicts a laser surgery and biopsy algorithm 500. Beginning at process block 504, a laser therapy assembly is secured to the channel laryngoscope's 10. At process block 508, the tip of the laser device is visible in the view on the monitor 320 and the laser aiming point is centered within the monitor 320. Thereafter, at process block 512, the channel laryngoscope 10 is placed into the mouth under direct vision of the user to obtain an image of the treatment area presented on the monitor viewable by the user. At process block 516, ventilation via engagement of the Jet Ventilation equipment is achieved. Finally, at process block 520, the laser therapy assembly and channel laryngoscope 10 is secured and lasing commenced of the treatment area.

Figure 35:
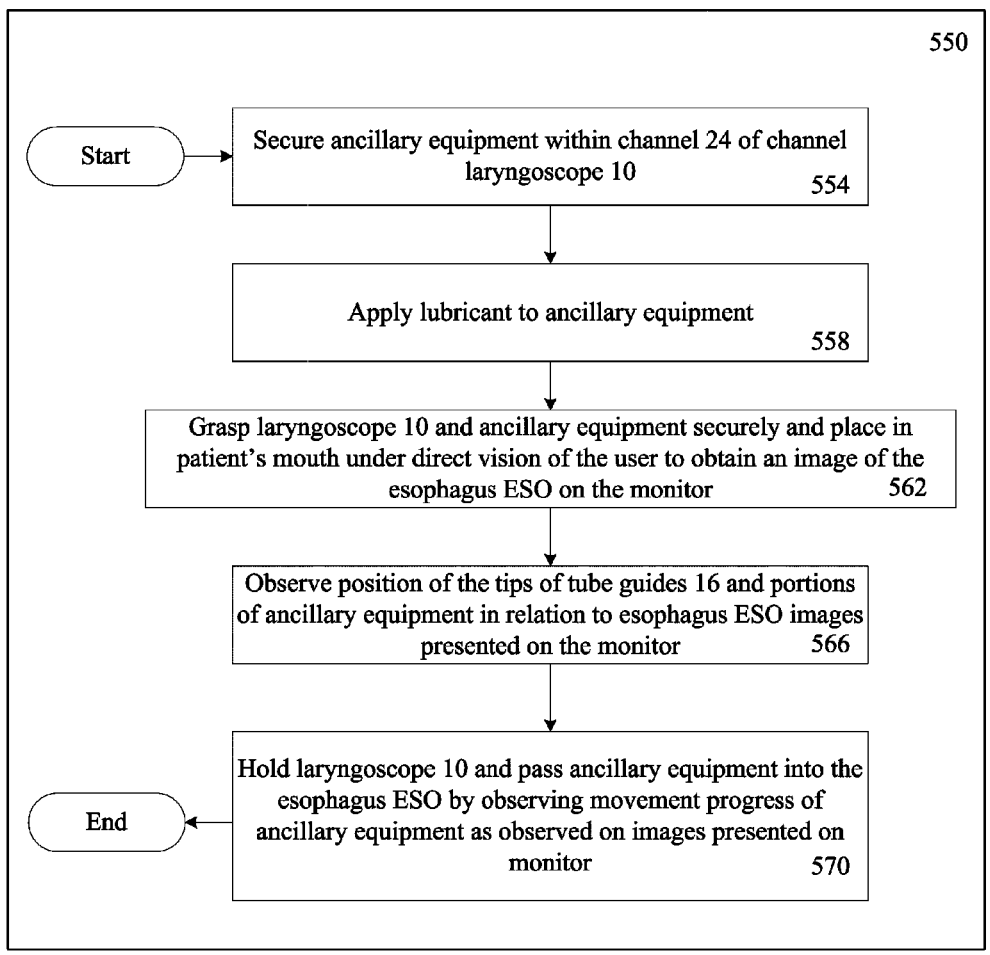

FIG. 35 depicts an ancillary equipment passage algorithm 550. Examples of ancillary equipment include Transesophageal Echo Probes and NasoGastric tubes. Beginning at process block 554, the ancillary equipment is secured within channel 24 of channel laryngoscope 10. Lubricant is applied to the ancillary equipment at process block 558. At process block 562, the channel laryngoscope 10 and secured ancillary is placed into the mouth under direct vision of the user. At process block 566, the tips of the tube guide 16 and portions of the ancillary equipment is viewed in esophagus ESO images presented on the monitor 320. At process block 570, the ancillary equipment, for example either a Transesophageal Echo Probe or a NasoGastric tube is placed within the esophagus ESO by images conveyed and displayed on the monitor 320.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. A laryngoscope sheath for insertion into the mouth, the sheath defining a proximal side and an anterior side, the anterior side generally contacts the tongue when the sheath is inserted into the mouth, comprising:
    a first ridge and a second ridge extending outwardly from the anterior side of the sheath and extending along the length of the sheath, the first ridge and second ridge defining an externally disposed channel;

a first tube guide located at the terminal end of the externally disposed channel and extending outwardly generally along the defined first ridge of the sheath;

a second tube guide at the terminal end of the externally disposed channel and extending outwardly generally along the defined first ridge of the sheath, and a spatula coupled to an anterior side of the second tube guide, the spatula extending outwardly from the second tube guide such that the spatula defines a plane that is generally parallel to a plane defined by the externally disposed channel and the spatula is configured to displace an epiglottis of a patient.

2. The laryngoscope sheath of claim 1, further comprising a video wand configured to be inserted into an interior channel defined by the sheath and sized to receive the video wand.

3. The laryngoscope sheath of claim 2 wherein the video wand further comprises:
a camera located at a video wand distal end; and
at least one light located at the video wand distal end.

4. The laryngoscope sheath of claim 3 wherein the sheath further comprises:
a window defined by the posterior of the sheath and located generally at the distal end of the anterior channel; and
a locking tab that extends proximally from the sheath proximal end that is configured to engage a video wand notch, such that when engaged the camera at the distal end of the video wand is aligned with the window of the sheath.

5. The laryngoscope sheath of claim 4 wherein the video wand defines one or more ridges extending along the anterior portion of the video wand and bracketing an anterior channel, the anterior channel configured to hold an endotracheal tube, such that the one or more ridges that extend along the anterior portion of the video wand are continuous with the one or more ridges that extend along the anterior portion of the sheath.

6. A laryngoscope comprising:
a video wand; and
a sheath that defines an interior channel sized to receive the video wand, the sheath further comprising:
one or more ridges extending along the anterior portion of the sheath, the one or more ridges bracketing an anterior channel that is configured to slideably engage an endotracheal tube; and
one or more tube guides extending distally from the ridges on the anterior portion of the sheath, the one or more tube guides configured to displace a patients epiglottis;
wherein when the video wand is inserted into the interior channel of the sheath and when the sheath and video wand are inserted into a patient with the one or more tube guides displacing a patients epiglottis, the sheath and video wand are configured to allow an endotracheal tube to be advanced along the anterior channel though the one or more tube guides causing the endotracheal tube to exit on a device posterior side and allowing the endotracheal tube to travel into the patients trachea,
wherein the video wand further comprises:
a camera located at a video wand distal end; and
at least one light located at the video wand distal end,
wherein the sheath further comprises:
a spatula coupled to an anterior side of a first tube guide of the one or more tube guides, the spatula extending outwardly from the second tube guide such that the spatula is generally defines a plane that is parallel to the plane defined by the anterior channel and is configured to displace a patients epiglottis a window defined by the posterior of the sheath and located generally at the distal end of the anterior channel; and
a locking tab that extends proximally from the sheath proximal end that is configured to engage a video wand notch, such that when engaged the camera at the distal end of the video wand is aligned with the window of the sheath.

7. The laryngoscope of claim 6 wherein the video wand defines one or more ridges extending along the anterior portion of the video wand and bracketing an anterior channel, the anterior channel configured to hold an endotracheal tube, such that the one or more ridges that extend along the anterior portion of the video wand are continuous with the one or more ridges that extend along the anterior portion of the sheath.

8. The laryngoscope of claim 7 wherein when the endotracheal tube is advanced the tube remains within the channel by the pressure exerted by the tongue against the anterior portion of the sheath and wand.

9. The laryngoscope of claim 8 wherein the video wand is flexible.

10. The laryngoscope of claim 9 wherein the sheath is at least one of straight, substantially straight, substantially curved, and curved.

11. The laryngoscope of claim 10 wherein, the video wand is fixedly attached to the sheath.

12. A method of operating a laryngoscope comprising:
securing a video wand into an internal chamber of a sheath by inserting a notch on the video wand into a locking tab located at a proximal end of the sheath, when the video wand is secured to the sheath, a camera at the distal end of the video wand is aligned with a window of the sheath; and
aligning an endotracheal tube with an anterior channel defined by the video wand and the sheath, the anterior channel originating at a video wand proximal end and terminating at one more tube guides that extend outwardly from the distal end of the sheath, the tube guides are generally configured to displace the epiglottis, the anterior channel is configured, when the sheath is inserted into a patient, to enable an endotracheal tube to be advanced along the anterior channel and through the tube guides and into a trachea.

13. The method of claim 12 wherein the video wand further comprises:
a camera located at a video wand distal end; and
at least one light located at the video wand distal end.

14. The method of claim 13 wherein the sheath further comprises a spatula coupled to an anterior side of a first tube guide of the one or more tube guides, the spatula extending outwardly from the first tube guide such that the spatula defines a plane that is parallel to a plane defined by the anterior channel and is configured to displace an epiglottis of a patient.

15. The method of claim 14 wherein the video wand defines one or more ridges extending along the anterior portion of the video wand and bracketing an anterior channel, the anterior channel configured to hold an endotracheal tube, such that the one or more ridges that extend along the anterior portion of the video wand are continuous with the one or more ridges that extend along the anterior portion of the sheath.

16. The method of claim 15 wherein the sheath is at least one of straight, substantially straight, substantially curved, and curved.

17. The method of claim 16 wherein, the video wand is fixedly attached to the sheath.

* * * * *